United States Patent [19]

Feigelson et al.

[11] Patent Number: 5,189,158
[45] Date of Patent: Feb. 23, 1993

[54] 4-SUBSTITUTED AZETIDINONES AS PRECURSORS TO 2-SUBSTITUTED-3-CARBOXY CARBAPENEM ANTIBIOTICS AND A METHOD OF PRODUCING THEM

[75] Inventors: Gregg B. Feigelson, Spring Valley; William V. Curran; Carl B. Ziegler, both of Pearl River, all of N.Y.

[73] Assignee: American Cyanamid Company, Wayne, N.J.

[21] Appl. No.: 672,496

[22] Filed: Mar. 20, 1991

[51] Int. Cl.$^5$ ............... C07D 487/00; C07D 487/04
[52] U.S. Cl. .................................... 540/302; 540/350
[58] Field of Search ........................... 540/302, 350

[56] References Cited

U.S. PATENT DOCUMENTS

| | | |
|---|---|---|
| 4,350,631 | 9/1982 | Christensen . |
| 5,051,502 | 9/1991 | Miller et al. ............ 540/302 |
| 5,055,573 | 10/1991 | Cama et al. ............ 540/350 |
| 5,064,954 | 11/1991 | Uyei et al. ............ 540/302 |
| 5,068,232 | 11/1991 | Ziegler et al. ............ 540/302 |
| 5,122,604 | 6/1992 | Sunagawa et al. ............ 540/350 |

FOREIGN PATENT DOCUMENTS

| | | |
|---|---|---|
| 83301073 | 9/1983 | European Pat. Off. . |
| 89102859 | 8/1989 | European Pat. Off. . |

OTHER PUBLICATIONS

March, Jerry, *Advanced Organic Chemistry*, John Wiley Sons, U.S.A., 1985 pp. 796–798.
Wasserman et al., Tetrahedron Letters, 25: 3747–3750 (1984).

*Primary Examiner*—Marianne M. Cintins
*Assistant Examiner*—Rebecca Cook
*Attorney, Agent, or Firm*—Kenneth J. Dow

[57] ABSTRACT

New 4-substituted azetidinones having the formulea I and II:

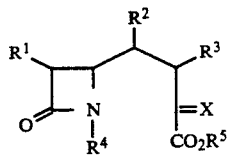

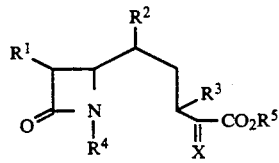

with $R^1$, $R^2$, $R^3$, $R^4$, $R^5$ and X defined hereafter, which are intermediates for the preparation of carbapenem and carbacephem antibacterials and processes for producing such antibacterials through the utilization of an acid mediated ring closure reaction.

2 Claims, No Drawings

4-SUBSTITUTED AZETIDINONES AS PRECURSORS TO 2-SUBSTITUTED-3-CARBOXY CARBAPENEM ANTIBIOTICS AND A METHOD OF PRODUCING THEM

BACKGROUND OF THE INVENTION

1. Field of the Invention

The invention relates to new 4-substituted azetidinones having the formulae I and II:

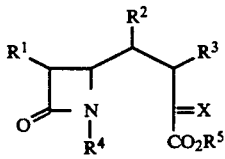

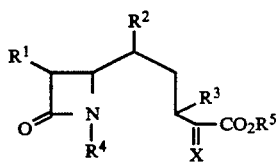

with $R^1$, $R^2$, $R^3$, $R^4$, $R^5$ and X defined hereafter, as intermediates for the preparation of carbapenem and carbacephem antibacterials through the utilization of an acid mediated ring closure reaction shown to form carbapenems III and carbacephems IV with $R^1$–$R^5$ defined hereafter.

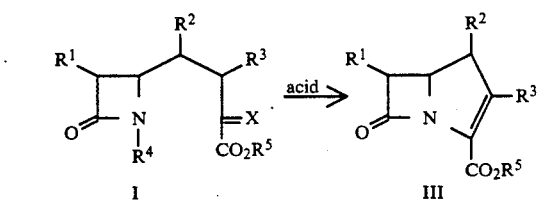

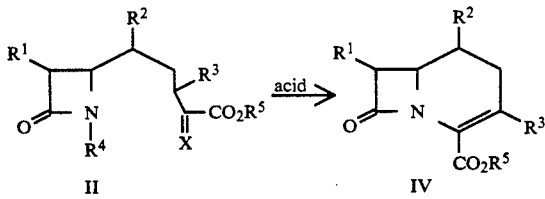

DESCRIPTION OF THE PRIOR ART

A number of carbapenem derivatives containing the basic structure (and numbering scheme)

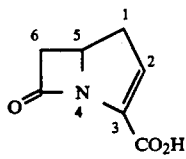

have been disclosed in the literature to have utility as antibacterial agents. The 2-substituted carbapenems are known to be effective antibacterials. For example, T. H. Salzmann et al., in "Regent Advances in the Chemistry of β-Lactam Antibiotics," P. H. Bentley and R. Southgate eds., Royal Society of Chemistry, 1989, pp. 171–189 discloses 2-alkyl-3-carboxycarbapenems

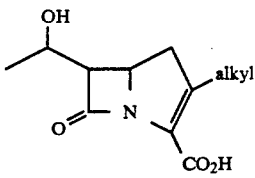

to have antibacterial activity where alkyl is defined therein. R. B. Sykes et al., in "Antibiotic Inhibitors of Bacterial Cell Wall Biosynthesis," D. J. Tipper ed., Pergamon Press, 1987, pp. 184–188 describes 2-substituted-3-carboxy carbapenems

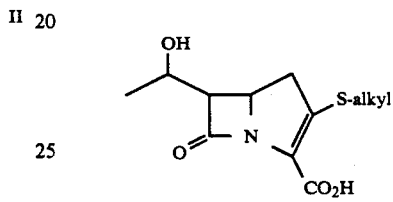

having antibacterial activity, where S-alkyl is defined therein.

In U.S. Pat. No. 4,707,547 2-amino-substituted 3-carboxy carbapenems

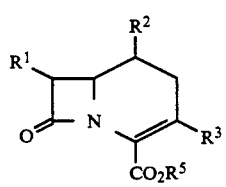

are disclosed to have antibacterial properties, where amine is defined therein. 2-Substituted-3-carboxy carbapenems that have substituents bonded to the 2-position of the carbapenem ring through carbon, sulfur or nitrogen all have antibacterial properties of interest.

General methods to prepare the carbapenem nucleus are limited. In U.S. Pat. No. 4,350,631 a rhodium (II) acetate catalyzed ring closure of the α-diazo-β-ketoester produces the 2-oxo-3-carboxy carbapenem nucleus. This product serves as a key intermediate for the preparation of other 2-substituted-3-carboxy carbapenems.

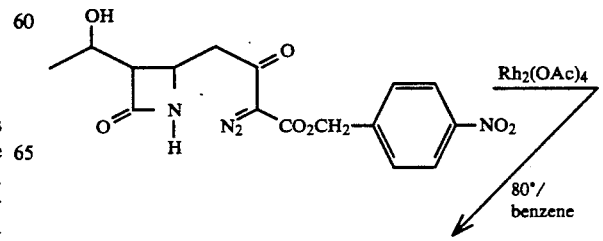

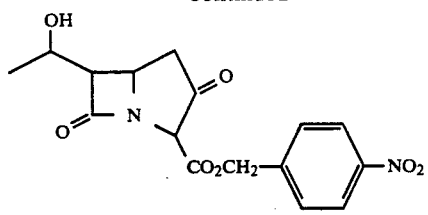

Another general method to synthesize the carbapenem nucleus is found in European Patent Application No. 83301073.9 (Beecham). The carbapenem nucleus is synthesized via an intramolecular Wittig reaction shown below using a specific example (2-thiopyrimidinyl-3-carboxy carbapenem) from this disclosure. This intramolecular Wittig reaction method is also used to prepare 2-alkylsubstituted-3-carboxy carbapenems as demonstrated in European Patent Application No. 89102859.9 (Fujisawa).

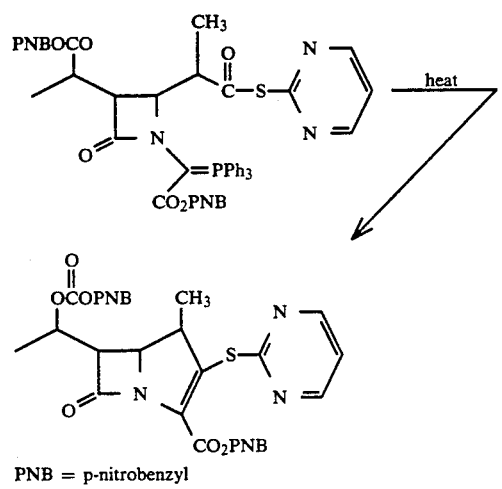

PNB = p-nitrobenzyl

H. Wasserman et al., reported in *Tetrahedron Letters*, Vol. 25, pp. 3747–3750, (1984) a method to make a known carbapenem and carbacepham from the earlier mentioned U.S. Pat. No. 4,350,631. In this disclosure a diketoester is closed to form a 3-hydroxy carbapenem via dehydration with activated molecular sieves. The hydroxyl group in this intermediate must be removed in a reduction step to form the β-ketoester carbapenem that is disclosed in the Merck patent. The Wasserman et al. disclosure provides no teaching or suggestion on the preparation of compounds with general formulae I or II where $R^3$ is a functionality other than the oxo group utilized therein. Additionally, the Wasserman et al. disclosure provides no teaching for the direct conversion of compounds with formulae I and II to cyclized adducts III and IV respectively.

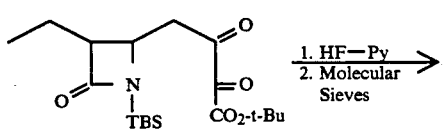

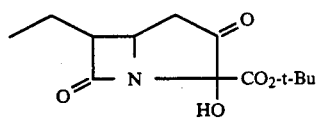

The object of the present invention is two-fold. The first objective is to provide novel families of 4-substituted azetidinones of formulae I and II via new and general chemical processes. The second objective is to demonstrate the utility of compounds I and II as precursors in a one-step acid mediated cyclization to carbapenem and carbacephem of formulae III and IV respectively.

SUMMARY OF THE INVENTION

It has now been found that 4-substituted azetidinones of formulae I and II are synthetic precursors to substituted carbapenems III

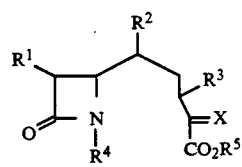

I

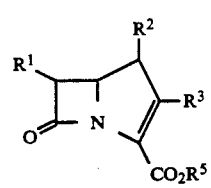

II and carbacephems IV respectively via an acid mediated ring closure reaction.

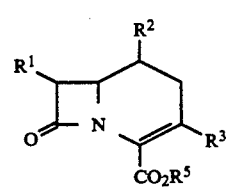

III

IV

In the above formulae I–IV:

$R^1$ is hydrogen, hydroxy (lower) alkyl or protected hydroxy (lower) alkyl. Suitable hydroxy (lower) alkyl substituents may include straight or branched lower alkyl having a hydroxyl group such as hydroxymethylene, 2-hydroxyethyl, hydroxypropyl, 1-hydroxyethyl. Suitable protected hydroxy (lower) alkyl means the aforementioned hydroxy (lower) alkyl in which the hydroxy group is protected by a conventional hydroxy protective group. Preferable protecting groups are, the trisubstituted silyl such as trimethylsilyl, triethylsilyl, tert-butyldimethylsilyl, tert-butyldiphenylsilyl; an acyloxy group such as a lower aliphatic acyloxy group preferably allyloxycarbonyloxy or an aralkyloxycarbonyloxy group preferably benzyloxycarbonyloxy or 4-nitrobenzyloxycarbonyloxy. Other suitable examples of $R^1$ can be found in U.S. Pat. No. 4,921,852.

$R^2$ is hydrogen or substituent groups previously disclosed for other carbapenem derivatives. More specifically, $R^2$ may be hydrogen or any of the non-hydrogen 1-substituents disclosed for example, or in U.S. Pat. No. 4,350,631. Preferred non-hydrogen $R^2$ substituents include ($C_1$-$C_6$) alkyl, most preferably, methyl, phenyl and phenyl ($C_1$-$C_6$) alkyl. The non-hydrogen $R^2$ substituent may be in either $\alpha$- or $\beta$-configuration, and it is intended that the present invention include the individual $\alpha$- and $\beta$-isomers, as well as mixtures thereof. The most preferred 1-substituted compounds are those having the $\beta$-configuration, especially those having the $\beta$-methyl substituent;

$R^3$ is hydrogen, any suitable leaving group, azido, an organic group bonded via sulfur, nitrogen, oxygen, phosphorus and carbon atom such as, but not limited to, F, Cl, Br, I, $OCOCH_3$, $OCOCF_3$, $OP(O)(OPh)$, $OSO_2CH_3$, $OSO_2Ph$, CN, $NO_2$;

$R^3$ may also be a moiety of the formula: $S(O)_iR^a$ wherein i is 0, 1, 2 and $R^a$ is an organic group bonded via a carbon atom to the sulfur atom. The group $R^a$ may be hydrogen, ($C_1$-$C_6$) alkyl, ($C_3$-$C_7$) cycloalkyl, ($C_2$-$C_6$) alkenyl, ($C_2$-$C_6$) alkenyl, aryl, heteroaryl, aryl ($C_1$-$C_6$) alkyl, heteroaryl ($C_1$-$C_6$) alkyl, ($C_1$-$C_6$) alkanoyl, arylcarbonyl, heteroarylcarbonyl, heterocyclyl, heterocyclyl ($C_1$-$C_6$) alkyl, fused heterocyclyl, fused heteroaryl ($C_1$-$C_6$) alkyl, fused heteroaryl fused heterocyclyl ($C_1$-$C_6$) alkyl, quaternized heteroaryl quaternized heteroaryl ($C_1$-$C_6$) alkyl, quaternized heterocyclyl, quaternized heterocyclyl, ($C_1$-$C_6$) alkyl, quaternized fused heterocyclyl, quaternized fused heterocyclyl ($C_1$-$C_6$) alkyl, quaternized fused heterocyclyl, quaternized fused heteroaryl ($C_1$-$C_6$) alkyl, quaternized heterocyclyl ($C_1$-$C_6$) thioalkyl, any of such groups being optionally substituted. Suitably, the heteroatom or heteroatoms in the above-named heterocyclyl, fused heterocyclyl, heteroaryl and fused heteroaryl moieties are selected from 1–4 oxygen, nitrogen or sulfur atoms and each ring of the heterocycle, fused heterocycle, heteroaryl, and fused heteroaryl moieties is comprised of up to 7 atoms, preferably 5 or 6 atoms. The heteroatom or heteroatoms in the above-named quaternized heteroaryl, quaternized heteroaryl ($C_1$-$C_6$) alkyl, quaternized heterocyclyl, quaternized heterocyclyl ($C_1$-$C_6$) alkyl, quaternized fused heterocyclyl, quaternized fused heterocyclyl ($C_1$-$C_6$) alkyl, quaternized fused heteroaryl, quaternized fused heteroaryl ($C_1$-$C_6$) alkyl, and quaternized heterocyclyl ($C_1$-$C_6$) thioalkyl moieties are selected from 1–4 oxygen, nitrogen or sulfur atoms and must contain at least one nitrogen atom and each ring of the respective moiety is comprised of 5 or 6 atoms.

Optional substituents for the group $R^a$ include $C_1$-$C_6$ alkyl, amino, $C_1$-$C_6$ alkanoylamino, mono-, di- and tri-($C_1$-$C_6$) alkylamino, hydroxy, $C_1$-$C_6$ alkoxy, mercapto, $C_1$-$C_6$ alkylthio, heteroarylthio, fused heteroarylthio, arylthio, heterocyclylthio, fused heterocyclylthio, sulphamoyl, carbamoyl, amidino, guanidino, nitro, fluoro, chloro, bromo, carboxy and salts and esters thereof, $C_1$-$C_6$ alkanoyloxy, arylcarbonyl, heteroarylcarbonyl, heterocyclylcarbonyl, fused heterocyclylcarbonyl.

Suitably, $R^a$ is $C_1$-$C_6$ alkyl for example methyl, ethyl or isopropyl, optionally substituted by amino, $C_1$-$C_6$ alkanoylamino, carboxy, mono- and dialkylamino hydroxy amidino or $C_1$-$C_6$ alkoxy. Preferably, $R^6$ is ethyl-substituted by $C_1$-$C_6$ alkanoylamino, for example $R^6$ is acetamidoethyl.

Suitably, $R^a$ is $C_2$-$C_6$ alkenyl and, in particular, optionally substituted vinyl wherein the substituents are selected from those described hereinbefore. Preference is given to $C_1$-$C_6$ alkanoylamino such as acetamido, carbamoyl groups including mono- and di-$C_1$-$C_6$ alkyl carbamoyl, such as phenylcarbamoyl and $NH_2CO$—, a carboxy group where the carboxy group is esterified with an alkyl ester such as methyl or as its araalkyl ester such as 4-nitrobenzyl ester or the carboxy group is salified as its sodium or potassium salt.

Suitably, $R^a$ is aryl such as phenyl; aralkyl wherein the aryl moiety is phenyl and the alkyl moiety is 1 to 6 carbon atoms such as benzyl or phenethyl. In particular, $R^a$ may be optionally substituted aralkyl wherein the substituents for $C_1$-$C_6$ alkyl portion is hereinabove defined and optional substitution for the phenyl ring consists of one or more of the following substituents; amino, $C_1$-$C_6$ alkanoylamino, mono- and di-alkylamino, hydroxy, amidino or $C_1$-$C_6$ alkoxy, sulphanoyl, carbamoyl, nitro, chloro, fluoro, bromo, carboxy and salts and esters thereof. Suitable examples of the above-named list are:

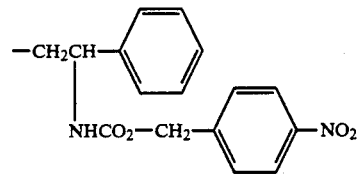

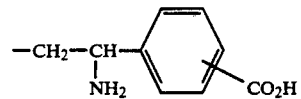

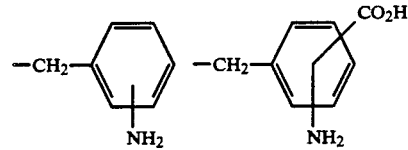

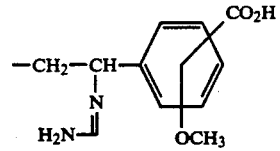

Suitably, $R^a$ is $C_1$-$C_6$ alkanoyl such as —$CH_2$—$CH_2$-$C(O)CH_3$ or —$CH_2C(O)(CH_2CH_3$ optionally substituted by $C_1$-$C_6$ alkanoylamino, carboxy and salts and esters thereof, dialkylamino, hydroxy, amidino, sulphamoyl, carbamoyl, fluoro, chloro, bromo. Suitable examples of the above named list include:

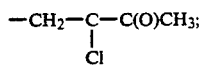
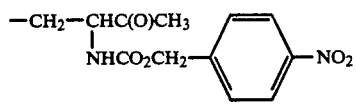
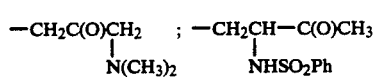

Suitably, $R^a$ is heteroaryl where the heteroatom or heteroatoms in the heterocycle are selected from 1–4 oxygen, nitrogen or sulfur atoms such as pyridinyl, furanyl, imidazolyl, thiazolyl, triazolyl; heteroaryl ($C_1$–$C_6$) alkyl such as:

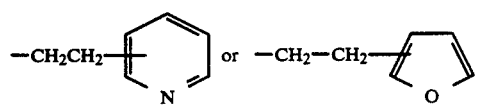

wherein the alkyl portion is optionally substituted as hereinabove described and the heteroaryl portion is optionally substituted with substituents hereinabove fined. Suitable examples are:

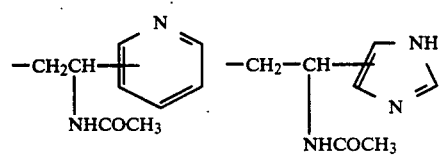

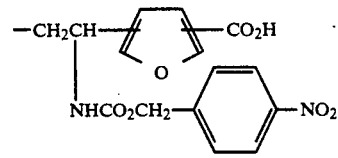

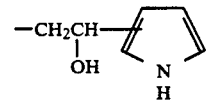

Suitably, $R^a$ is fused heteroaryl where the heteroatom or heteroatoms of the heteroaryl ring are selected from 1–4 oxygen, nitrogen or sulfur atoms and optionally substituted as hereinabove described. Preferable examples are the [3.3.0] and [3.4.0] fused bicyclic heteroaryl ring system generically shown:

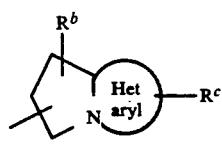

where the definitions of $R^b$ and $R^6$ as well as the classes of fused ring systems are disclosed in European Patent Application No. EPO 368 259 A1 (Daiichi).

Suitably, $R^a$ is a quaternized fused heteroaryl where the heteroatoms of the heteroaryl ring are selected from 1 to 4 nitrogens and optionally substituted as herein-above described. Preferable examples are the [3.3.0], [3.4.0], [4.3.0] and [4.4.0] quaternized fused heteroaryl rings, optionally substituted with an acidic substituent. Suitable examples are shown:

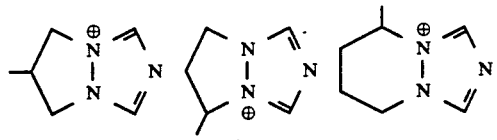
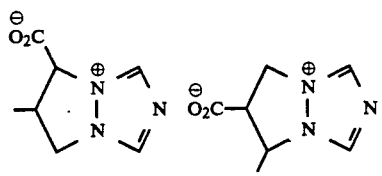
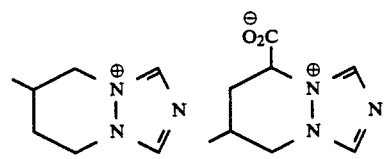
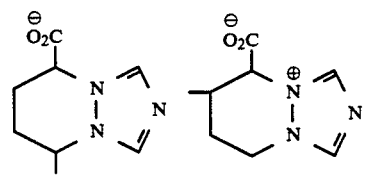
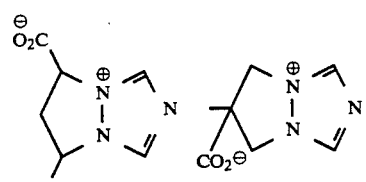
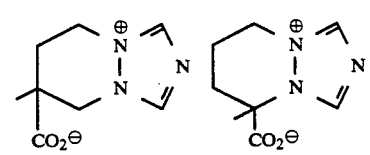
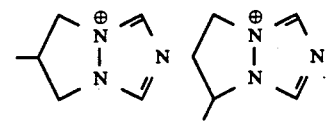
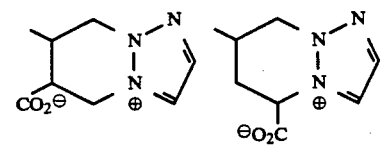
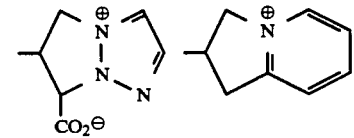

-continued

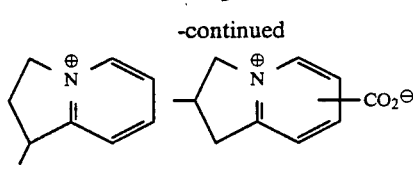

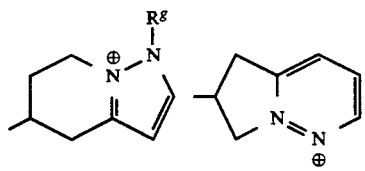

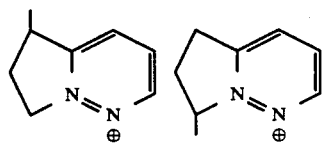

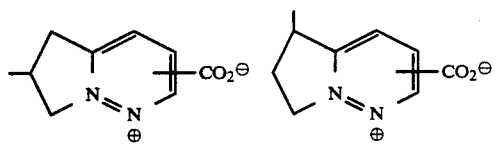

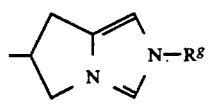

Another suitable example of quaternized heteroaryl (C$_1$-C$_6$) alkyl group is shown generically as:

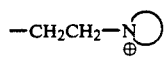

where the definition of the heteroaryl moiety:

is disclosed in U.S. Pat. No. 4,952,397. Other suitable examples of quaternized heterocyclyl (C$_1$-C$_6$) alkyl groups are quaternized heterocyclyl (C$_1$-C$_6$) thioalkyl groups such as:

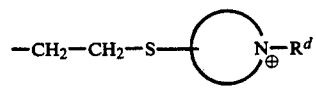

wherein the definition of the heteroaryl ring:

and the definition of the alkyl group R$^d$ is disclosed in U.S. Pat. No. 4,880,922.

Suitably, R$^a$ is heterocyclyl where the heteroatom or heteroatoms in the heterocycle are selected from 1 to 4 oxygen, nitrogen or sulfur atoms. Additionally, the above mentioned heterocyclyl moiety is optionally substituted with one or more of the following substituents hereinabove defined. Preferred examples of the above named list are substituted pyrolidinyl groups of formula:

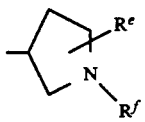

where the definition of R$^e$ and R$^f$ are found in U.S. Pat. No. 4,921,852, U.S. Pat. No. 4,963,543, U.S. Pat. No. 4,463,544 and U.S. Pat. No. 4,740,507; substituted proline derivatives as:

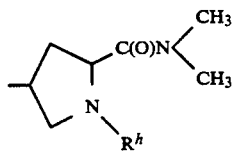

where R$^h$ is defined in U.S. Pat. No. 4,888,344 or pyrazolidinyl substituents preferably:

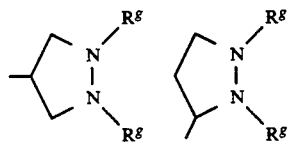

where R$^g$ is hydrogen, tert-butyldimethylsilyl or other suitable tri-substituted silyl group, —CO$_2$CH$_2$—(4-nitrophenyl), —CO$_2$CH$_2$CH=CH$_2$.

R$^3$ may also be OH, or OR$^a$ where is hereinabove defined;

R$^3$ may also be an organic residue bonded via a nitrogen atom. Suitable substituents can be represented as: —NC, NCO, —NHCN, NR$^h$R$^i$ where R$^h$ and R$^i$ are independently selected from hydrogen; substituted or unsubstituted alkyl and cycloalkyl having from 1 to 8 carbon atoms, aryl, araalkyl, such as phenyl (C$_1$-C$_4$) alkyl and heterocycle, heterocyclyl (C$_1$-C$_4$) alkyl, heteroaryl and heteroaryl (C$_1$-C$_4$) alkyl wherein the heteroatom or heteroatoms are selected from oxygen, nitrogen and sulfur, and a cyclic group wherein R$^h$ and R$^i$ are joined; and wherein the ring or chain substituent or substituents on R$^h$, R$^i$ or the cyclic radical formed by their joinder are selected from the group consisting of amino, mono-, di- and tri (C$_1$-C$_6$) alkylamino, hydroxyl, carboxyl, alkoxyl, chloro, fluoro, bromo, nitro, —SO$_2$NH$_2$, phenyl, benzyl and alkoxylcarbonyl and carboxamido.

Relative to the above generic description for —NR$^h$R$^i$, the disclosure U.S. Pat. No. 4,707,547, pp. 3–4 contains specific representative examples. Other suitable substituents are hydroxylamino, hydrazinyl and iminyl shown —N(R$^h$)OR$^i$, N(R$^h$)NR$^h$R$^i$,

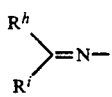

wherein $R^h$ and $R^i$ are hereinabove defined, acyl amino groups of the formulae:

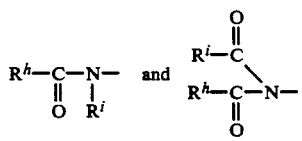

wherein $R^h$ and $R^i$ are hereinabove defined; groups represented by the formula:

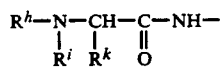

wherein $R^k$ represents hydrogen, substituted or unsubstituted ($C_1$-$C_3$) alkyl* (in the description of respective groups in the present specification, groups marked with an asterisk may have a substituent as assigned hereinabove for $R^h$ and $R^i$), ($C_2$-$C_6$) alkenyl*, ($C_2$-$C_6$) alkynyl*, heterocyclyl* and heteroaryl* wherein the heteroatom or heteroatoms are selected from 1-4 oxygen, nitrogen or sulfur and the cyclic portion has 5 or 6 ring atoms; groups represented by the formula:

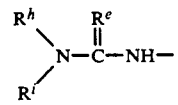

where $R^h$ and $R^i$ are hereinabove defined and $R^e$ is oxygen and sulfur; groups represented by the formula:

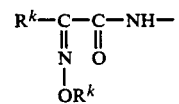

wherein $R^k$ is hereinabove defined; groups of the formula:

wherein $i=0, 1, 2$ and $R^a$ is hereinabove defined; groups represented by the formulae:

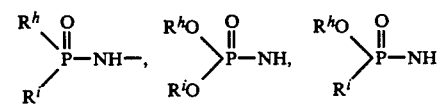

wherein $R^h$ and $R^i$ are hereinabove defined.

Representative examples of an acylamino group of the formulae:

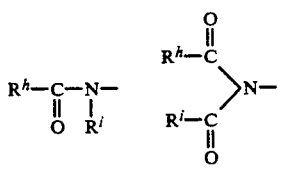

from the above-mentioned groups are: formylamino, acetylamino, isobutylrylamino, benzyloxycarbonylamino, 1-aminocyclohexcarbonylamino, 2-(2-amino-4-thiazolyl)-2-ethylideneacetylamino, 4-bromobenzoylamino, nicotinoylamino, 3-phenyl-5-methylisoxaxol-4-yl-carbonylamino, pyrrolidinone, succinimidoyl and maleimidoyl.

Representative examples of an acylamino group of the formula:

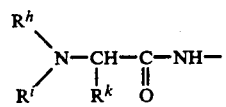

from the above-mentioned groups are:

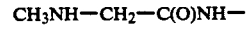

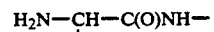

CH$_3$CH$_2$NH—CH(CH$_3$)C(O)NH—

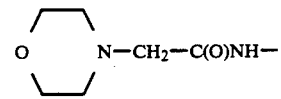

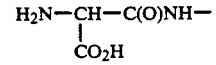

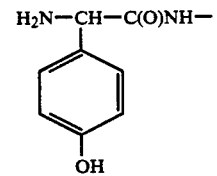

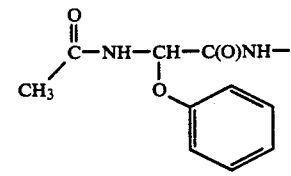

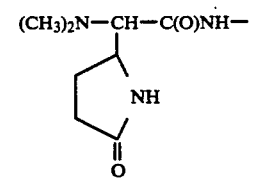

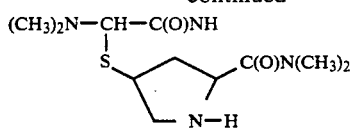
Representative examples of an acylamino group of the formula:
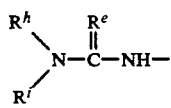
from the above-mentioned groups are:
H₂N—C(O)NH—
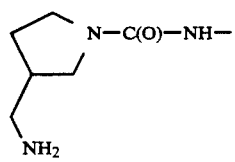
CH₃NHC(O)NH—
H₂N—C(S)NH—
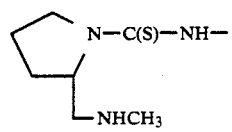
CH₃NH—C(S)NH—
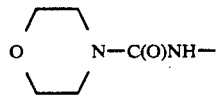
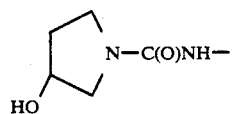
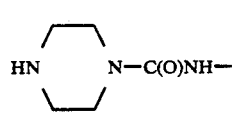
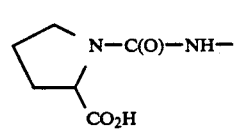
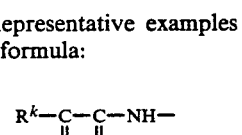
Representative examples of an acylamino group of the formula:
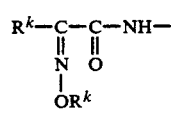
from the above-mentioned groups are:
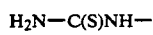
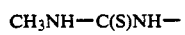
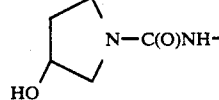
Representative examples of groups of the formula:
R$^a$S(O)$_i$NH—
from the above-mentioned listings are:
CH₃SO₂NH— 
C₆H₅SO₂NH— 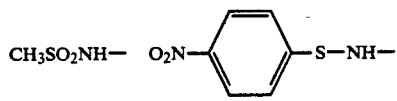
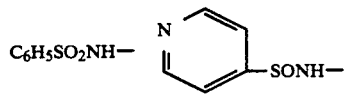
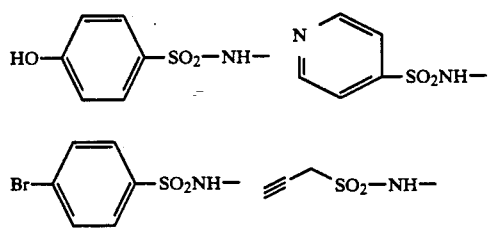

-continued

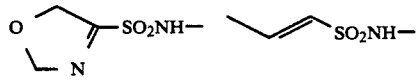

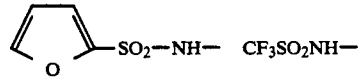

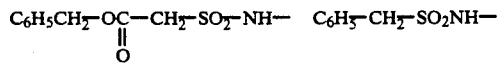

Representative examples of groups of the formula:

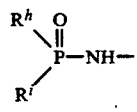

from the above-mentioned listings are: dimethylphosphoamino, diethylphosphoamino, diisopropylphosphoamino, diphenylphosphoamino, dibenzylphosphoamino.

Representative examples of the formula:

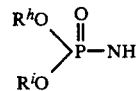

from the above-mentioned listings are:

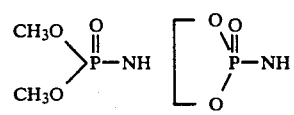

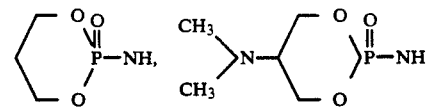

Representative examples of the formula:

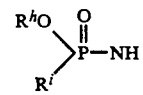

from the above-mentioned listings are:

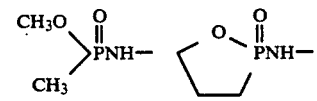

-continued

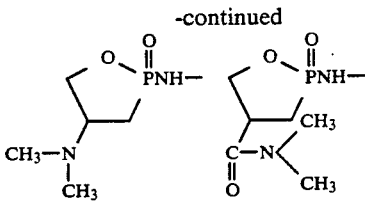

Representative examples of groups of the formula:

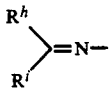

from the above-mentioned listings are:

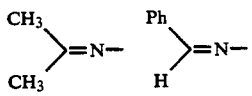

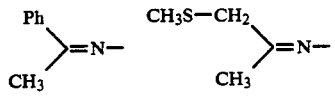

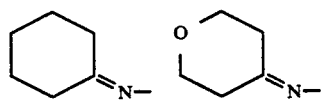

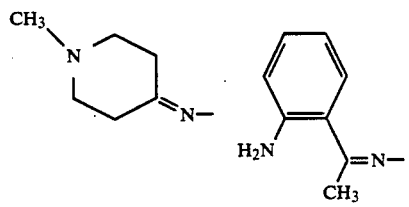

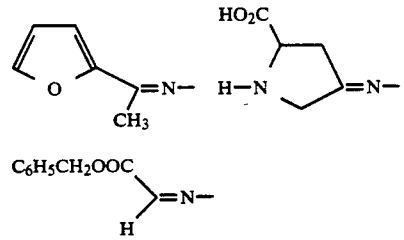

Representative examples of groups with the formula:

—N(R$^h$)OR$^i$ from the above-mentioned listings are: —NHOH, —N(CH$_3$)OH, —N(CH$_3$)OCH$_3$, —N(CH$_2$CH$_3$)OH, N(CH$_2$CH$_3$)OCH$_3$, —N(CH$_3$)OCH$_2$CO$_2$H, —N(CH$_3$)OCH$_2$CO$_2$CH$_2$C$_6$H$_5$, —N(CH$_3$)OC$_6$H$_5$,

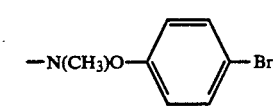

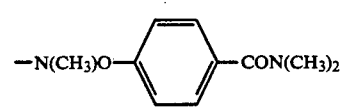

-continued
—N(CH₂CH=CH₂)OCH₃

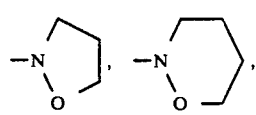

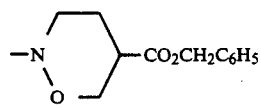

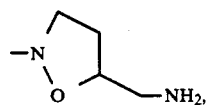

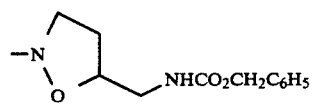

Representative examples of groups with the formula:
—N(R$^h$)NR$^h$R$^i$ from the above-mentioned listings are: —NH—NH₂, —N(CH₃)—NH₂, —N(CH₃)—NHCH₃, —NHN(CH₃)₂, —N(CH₃)N(CH₃)₂, —NHNHCO₂CH₂C₆H₅, —NHNHC₆H₅, —NHNHCH₂C₆H₅,

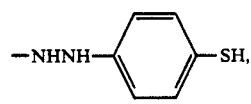

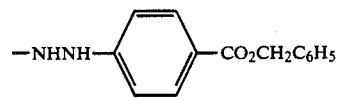

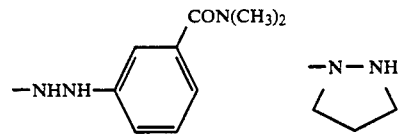

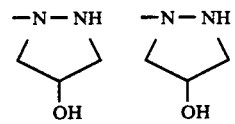

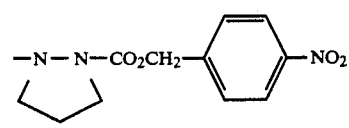

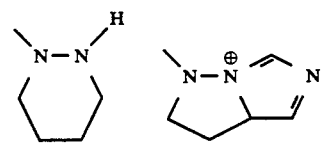

R³ may also be an organic residue bonded via a carbon atom. Suitably, the organic residue is bonded to either a bivalent, trivalent or tetravalent carbon.

Suitably, a bivalent carbon can be a nitrile

—C≡N or acetylenic, —C≡C—R$^a$ wherein R$^a$ is hereinabove defined. A trivalent carbon can be imino

wherein R$^a$, R$^h$ and R$^i$ are hereinabove defined. A tetravalent carbon can be $$-\underset{R^i}{\underset{|}{\overset{R^a}{\overset{|}{C}}}}-R^h$$

—CH₂F, —CH₂Cl, —CH₂Br, —CH₂I, —CH₂OCOCH₃, —C(O)NR$^h$R$^i$, —CHR$^k$NR$^i$R$^h$, —CHR$^k$N(R$^h$)OR$^i$, —CHR$^k$N(R$^k$)NR$^h$R$^i$, —CHF₂, —CHCl₂, —CH(Cl)CO₂H, —CHR$^k$N(R$^k$)C(O)NR$^h$R$^i$, —CHR$^k$C(NOR$^k$C(O)NR$^h$R$^i$, —CHR$^k$NHSO₂R$^k$, —CHR$^k$NHP(O)(OR$^i$)OR$^h$), —CHR$^k$P(O)(OR$^h$)(OR$^i$)
wherein R$^a$, R$^h$, R$^i$ and R$^k$ are hereinabove defined.

Representative examples of a bivalent carbon are:

—CN, —C≡C—H, —C≡C—CH₃,

—C≡C—CH₂OH

—C≡C—C₆H₅, —C≡C—CH₂NHCO₂—C(CH₃)₃

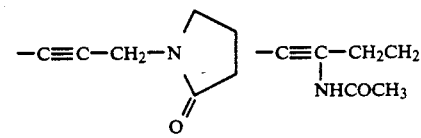

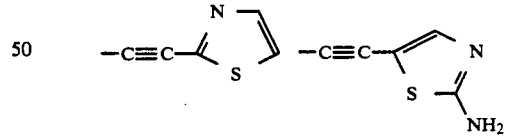

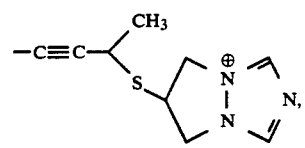

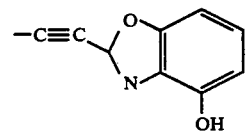

Representative examples of a trivalent carbon are:

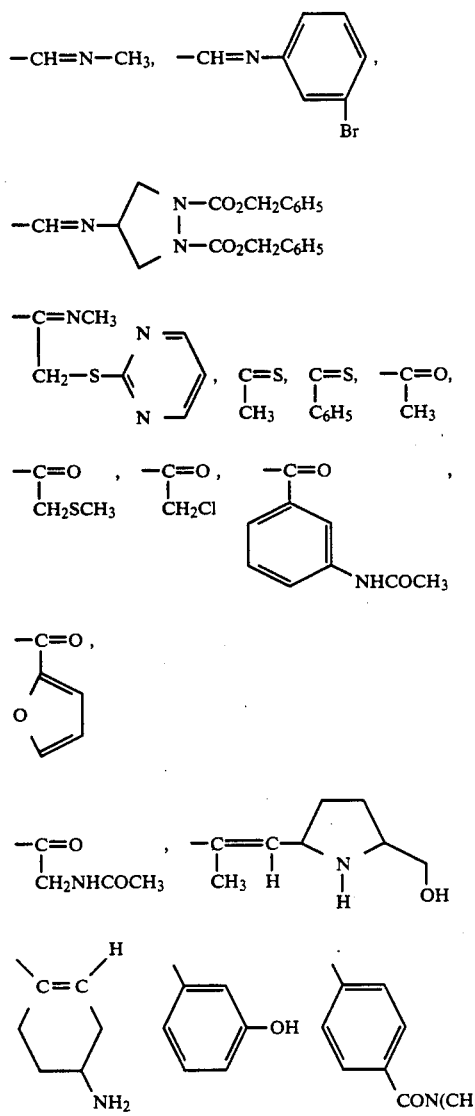
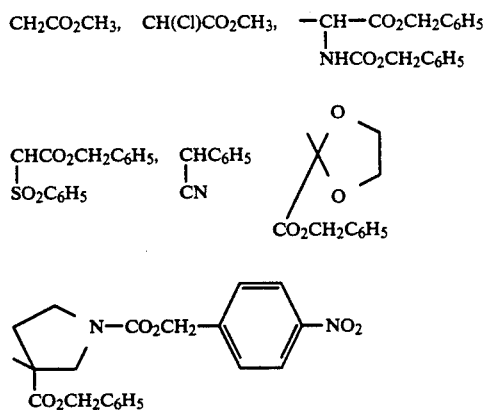

Representative examples of a tetravalent carbon are:

$R^3$ may also be an organic residue bonded via a phosphorus atom. Suitably, such groups can be represented as

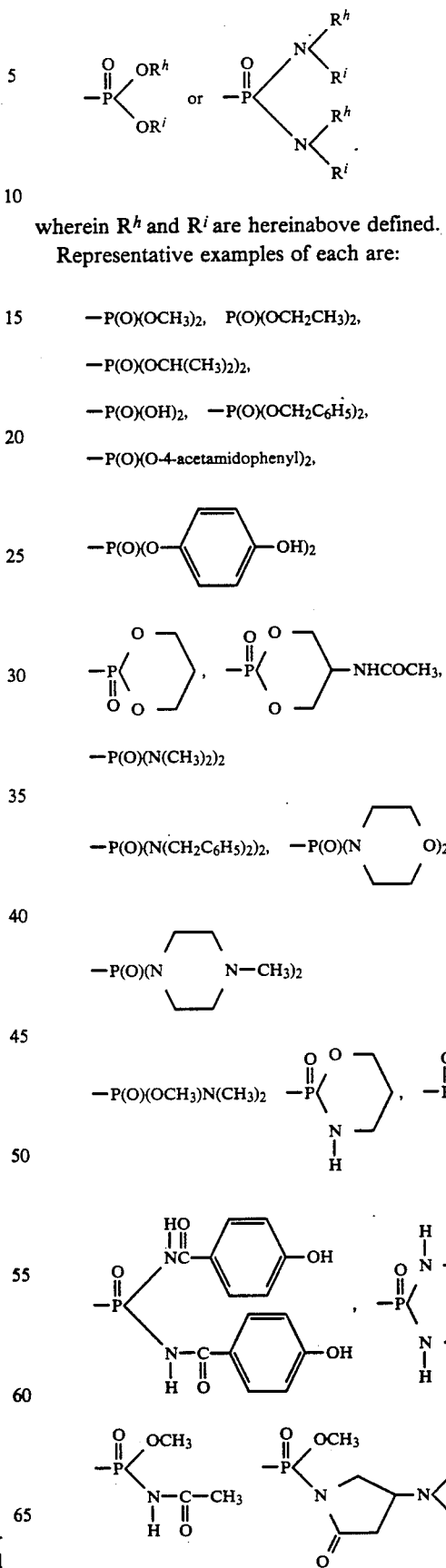

wherein $R^h$ and $R^i$ are hereinabove defined. Representative examples of each are:

—P(O)(OCH$_3$)$_2$, P(O)(OCH$_2$CH$_3$)$_2$,

—P(O)(OCH(CH$_3$)$_2$)$_2$,

—P(O)(OH)$_2$, —P(O)(OCH$_2$C$_6$H$_5$)$_2$,

—P(O)(O-4-acetamidophenyl)$_2$,

—P(O)(N(CH$_3$)$_2$)$_2$

—P(O)(N(CH$_2$C$_6$H$_5$)$_2$)$_2$,

—P(O)(OCH$_3$)N(CH$_3$)$_2$

-continued

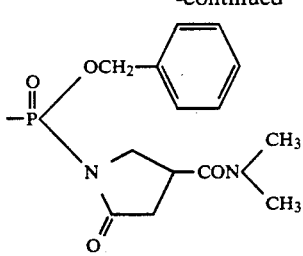

$R^4$ is hydrogen or a readily removable protecting group for an amide nitrogen such as, but not limited to, trisubstituted silyl, preferable groups are trimethylsilyl, triethylsilyl, triisopropylsilyl, tert-butyldimethylsilyl, and tert-butyldiphenylsilyl;

$R^5$ is hydrogen or a suitable carboxy protecting group that can readily be removed. Preferable examples are a straight-chain or branched lower alkyl group such as methyl, ethyl, n-propyl, tert-butyl; a lower haloalkyl group such as 2,2,2-trichloroethyl; a lower alkoxymethyl group such as methoxymethyl, ethoxymethyl, a lower aliphatic acyloxymethyl group such as acetoxymethyl, isobutyryloxymethyl, or pivaloyloxymethyl; a 1-(lower alkoxy)carbonyloxyethyl group such as 1-methoxycarbonyloxyethyl, 1-ethoxycarbonyloxyethyl, an aralkyl group such as benzyl, p-methoxybenzyl, o-nitrobenzyl, or p-nitrobenzyl; a benzhydryl group; a phthalidyl group, a silyl such as trimethylsilyl or t-butyldimethylsilyl or 2-trimethylsilylethyl; an allylic group such as allyl, 2-chloro-2-propenyl, 2-butenyl, 3-methyl-2-butenyl or 2-cinnamyl;

X is selected from oxygen, sulfur or a group that is hydrolytically equivalent to oxygen. Suitable groups that are hydrolytically equivalent to oxygen can be represented as; imines, $X=NR^6$, where $R^6=H$, a straight-chain or branched $(C_1-C_6)$ lower alkyl group such as methyl, ethyl, n-propyl, isopropyl, n-butyl, isobutyl, a trialkylsilyl group such as tert-butyldimethylsilyl; an oxime, $X=NR^7$, where $R^7$ is OH, a straight or branched lower alkoxy group such as methoxy, ethoxy, n-propoxy, isopropoxy, n-butoxy, iso-butoxy, sec-butoxy or tert-butoxy; silyloxy groups such as trimethylsilyloxy, tert-butyldimethylsilyloxy, phenyldimethylsilyloxy or phenyldi-tert-butylsilyloxy.

Relative to the above description, X can represent a hydrazone where $X=N-NR^8R^9$, where $R^8$ and $R^9$ are independently chosen from hydrogen, lower alkyl $(C_1-C_6)$, benzyl, phenyl, $CO_2R^5$ wherein $R^5$ is as hereinbefore defined or $R^8$ and $R^9$ together with the associated nitrogen form a 5 or 6 membered cycloalkyl ring. The following examples are representative for $N-NR^8R^9$: $N-NH_2$, $NNHCH_3$, $NNHCH_2CH_3$, $NNHCH(CH_3)_2$, $NN(CH_3)_2$, $NN(CH_2CH_3)_2$, $NN[CH(CH_3)_2]_2$, N—1-pyrrolidinyl, N—1-piperidinyl, N—4-morpholinyl, $N-NH(C_6H_5)$, $N-N(CH_3)C_6H_5$, $N-N(C_6H_5)_2$, $N-NH(CH_2C_6H_5)$, $N-N(CH_2C_6H_5)_2$, $N-NH(CO_2$-tert-butyl), $N-NH(CO_2$-4-nitrobenzyl), $N-NH(CO_2CH_2C_6H_5)$, $N-N(CO_2CH_6H_5)_2$, $N-N($tertbutyldimethylsilyl$)_2$;

The carbapenems III and carbacephems IV of the present invention are produced by treating the novel 4-alkylsubstituted azetidinones I and II in an inert solvent such as tetrahydrofuran or methylene chloride with an appropriate acid such as hydrochloric acid and or titanium tetrachloride using a temperature range of $-70°$ C. to 50° C. with 0° to 40° being the usual optimal range. The contact times between reagents usually is in the range of 1 minute to 240 minutes depending on the particular substitution pattern of the azetidinone used.

DESCRIPTION OF THE PREFERRED EMBODIMENTS

Novel 4-alkylazetidinones I and II according to the present invention are produced according to the following reaction schemes:

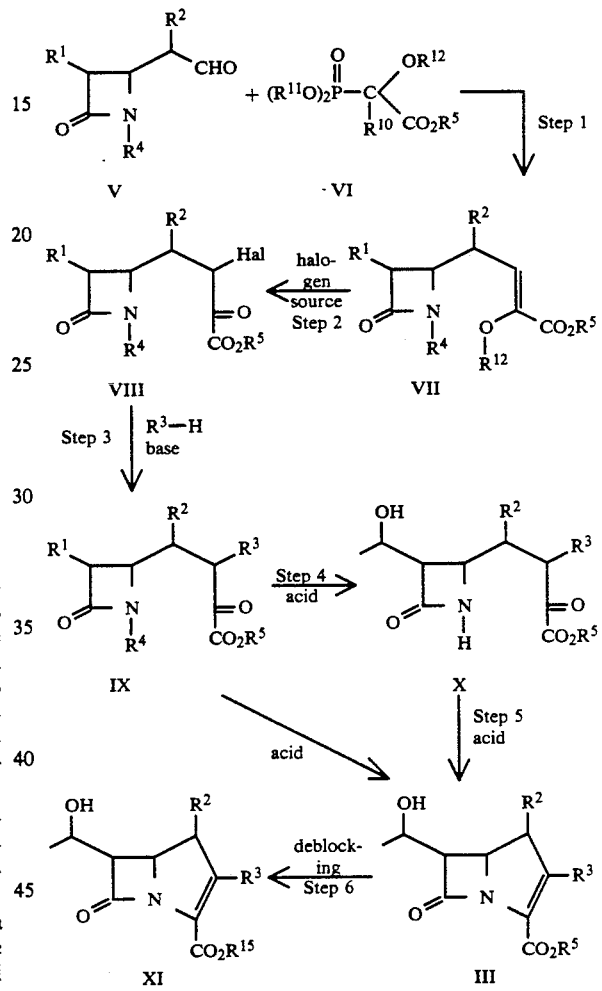

Scheme I

In Step 1 of Scheme 1, the aldehyde of formula V prepared by literature methods is contacted with the phosphonate anion VI to form the corresponding chain extended adduct VII wherein $R^1$, $R^2$, $R^4$ and $R^5$ are as defined hereinbefore and $R^{11}$ is alkyl or branched alkyl such as methyl, ethyl, propyl, iso-propyl, butyl, sec-butyl or tert-butyl; phenyl-substituted alkyl group such as benzyl or benzhydryl; phenyl, optionally substituted with 1-3 carbon groups such as methyl, ethyl and propyl. $R^{12}$ is a substituted silyl group such as trimethylsilyl or tert-butyldimethylsilyl; an acyl group such as a lower aliphatic acyl group such as acetyl, propionyl or an aralkylcarbonyl group such as benzylcarbonyl or 4-nitrobenzylcarbonyl. $R^{10}$ is a metal cation such as lithium, sodium or potassium. Preferred groups for $R^{11}$ and $R^{12}$ are methyl and tertbutyldimethylsilyl.

The aldehyde V and phosphonate anion VI of Scheme I can be reacted using those conditions of Nakamura in *Tetrahedron Letters*, vol. 22, pp. 663–666 (1981) as representative of this overall conversion.

In Step 2 of Scheme I, the vinyl ether adduct VII is treated with a suitable halogen source such as, but not limited to, bromine, N-bromosuccinimide, iodine, N-iodosuccinimide, N-chlorosuccinimide, with bromine being preferred, in the presence of a suitable solvent, such as, but not limited to, tetrahydrofuran, diethyl ether, dimethoxyethane, dioxane, toluene, methylene chloride with tetrahydrofuran being preferred. An excess of halogenation reagent is preferred relative to VII generally in the ratio of 1.1 equivalents of halogen source to one equivalent of the vinyl ether VII. Reaction concentrations usually are maintained in the range of 0.2 molar for the limiting reagent VII.

The vinyl ether substituted azetidinone VII in a suitable solvent can be treated with the suitable halogen source at temperatures ranging from −70° C. to 40° C. with a more narrow temperature range of −70° to 0° producing optimal results. Contact times of reagents usually are from 1 minute to 120 minutes with 5 to 10 minutes producing desired results.

The reaction product VIII, where $R^1$, $R^2$, $R^4$, $R^5$ are defined hereinabove and Hal=F, Cl, Br and I, is isolated after a sequence of conventional techniques in the art that include filtration, washing, chromatography and the like. Yields of halogenated product VIII are in the range of 60 to 95%.

In Step 3 of Scheme I, the halogen of the ketoester VIII is displaced with a suitable nucleophile $R^3$. The product Ketoester IX is formed on contacting VIII with the conjugate base of the species $R^3$—H in a suitable solvent and temperature range. The conjugate base of $R^3$—H is formed by treating $R^3$—H in a suitable anhydrous solvent such as tetrahydrofuran, dimethoxyethane, acetonitrile, dimethylformamide with a suitable base, such as, but not limited to, lithium, sodium or potassium bis(trimethylsilylamide), sodium hydroxide, sodium hydride, triethylamine, diisopropylethylamine, 1,8-diazobicyclo[5.4.0]undec-7-ene (DBU), alkyl lithiums such as methyl or butyl lithium at a temperature range of −70° C. to 20° C.

The halogenated ketoester VIII is then contacted with the performed conjugate base of $R^3$—H. The above process may be performed sequencially as described or in-situ where as a suitable base is contacted with the pair $R^3$—H and haloketoester VIII.

An excess of the conjugate base of reagent $R^3$—H relative to reagent VIII may be used and generally is preferred in the ratio of 1.1 to 1. Reaction concentrations usually are maintained in the range of 0.2 to 1.0 molar for the limiting reagent, VIII. The overall transformation described in Step 3 represents a conventional reaction type to one skilled in the art. A representative review of this reaction type is found in N. DeKimpe and R. Verhe in "The Chemistry of α-Haloketones, α-Haloaldehydes and α-Haloimines," S. Patai and Z. Rappaport eds., John Wiley & Sons 1988, pp. 1–368. The product IX of Step 3, Scheme I is isolated by conventional techniques in the art including dilute acid wash, dilution, filtration, aqueous washing, chromatography, crystallization and the like. Product yields range from 20 to 95%. In product IX, $R^1$-$R^5$ are hereinabove defined.

In Formula IX, $R^1$ and $R^4$ are independently selected from the list shown hereinabove. Preferred is where $R^1$ is 1-(tert-butyldimethyl)siloxyethyl, 1-(trimethylsiloxyethyl), 1-(allyloxycarbonyloxy)ethyl, 1-(benzyloxycarbonyloxy)ethyl or 1-(4-nitrobenzyloxycarbonyloxy)ethyl and where $R^4$ is tert-butyldimethylsilyl, trimethylsilyl or triethylsilyl. Removal of these types of protecting groups may be achieved by any number of conventional procedures such as acid hydrolysis for the silyl-based groups and catalytic reduction for the other two which are members of the carbonate-based protective groups.

In Step 4 of Scheme 1, the preferred 1-(tert-butyldimethyl)siloxyethyl group of $R^1$ and the tert-butyldimethylsilyl group of $R^4$ of ketoester IX are hydrolyzed to the 1-hydroxyethyl and N—H respectively via a standard procedure in the art that entail contacting keto ester IX with hydrogen fluoride in acetonitrile-water solvent. The generalized procedure of R. F. Newton et al., *Tetrahedron Letters*, (1979) no. 41, pp. 3981–3982 is followed here. Product X y8ields for this step range from 40–90% following conventional isolation techniques including neutralization with a weak base such as sodium bicarbonate dilution, extraction, washing with water, chromatography and crystallization. It is important to note that in some cases, depending on the nature of $R^1$ and $R^4$ in Formula IX, the acid deprotection of Step 4, Scheme I may not be necessary and the ketoester IX, therefore, is suited for ring closure which will now be discussed in Step 5 of Scheme I.

In Step 5 of Scheme I, compounds of the Formula X are contacted with an appropriate acid in a suitable solvent at temperatures of −100° C. to 40° C. While any suitable temperatures may be employed, it is preferred to use temperatures of −20° to 30° to eliminate undesired side reactions.

Suitable acids that can be employed in Step 5 generally are aqueous or non-aqueous and comprise the following:

titanium tetrachloride
titanium trichloride
titanium isopropoxide
titanium based acids with the generalized formulae Ti $A_y(OR^{13})_x$ where $R^{13}$ is an alkyl group which may be straight or branched chain having 1–4 carbon groups such as methyl, ethyl, n-propyl, isopropyl, n-butyl; phenyl-substituted alkyl groups such as benzyl. A is fluoride or chloride and x and y can have values of 0, 1, 2, 3 and 4 both the sum of x and y must always equal 4.
hydrochloric acid
hydrobromic acid
hydroiodic acid
sulfuric acid
nitric acid
trifluoroacetic acid
stannyl-based acids of the general formulae Sn $A_x$-$(OR^{13})_y$ where A, $R^{13}$, x and y are hereinabove defined.
iron trichloride
zirconium tetrachloride
boron trifluoride
hydrofluoroboric acid
zinc chloride, zinc bromide
magnesium halides including chloride bromide and iodide
aluminum based acids with general formulae Al $A_a(R^{14})_b$ where A is chloro or fluoro; $R^{14}$ is methyl, ethyl or propyl; a and b can have values ranging from 0 to 3 but the sum of a plus b must always equal 3.

Other strong acids which may be suitably employed are disclosed in "Modern Synthetic Reactions" by H. House, W. A. Benjamin, Inc. Menlo Park, Calif. 1972.

Suitable solvents and solvent combinations employed can be anhydrous or, at least in part, aqueous ones. Some suitable solvents and solvent combinations are:

tetrahydrofuran (THF) and THF/water
dimethoxyethane (DME) and DME/water
diethyl ether, diisopropyl ether
dioxane
acetone and acetone/water
acetonitrile and acetonitrile/water
methanol and methanol/water
ethanol and ethanol/water
propanol and isopropanol
benzene and toluene
N,N-dimethylformamide
N,N-dimethylacetamide
N-methylpyrrolidinone
acetic acid and acetic acid/water
trifluoroacetic acid
methylene chloride
chloroform
1,2-dichloroethane
carbon tetrachloride
ethyl acetate The solvent can be employed in amounts effective to solublize the ketoester X. Generally, solutions of X in the range of 0.05 to 2.0 molar are used in the acid mediated ring closure to form compounds of formula III, preferably a concentration of 0.15 to 0.5 molar is used.

The ketoester X in Step 5 of Scheme I can be contacted with a range of 1.1 to 5 equivalents of a suitable acid preferably 3 equivalents within a suitable temperature range of $-100°$ to $-40°$ C., preferably $-20°$ to $0°$ for time periods ranging from 0.02 hours to 1 hour preferably 0.15 hours under an inert atmosphere of argon or nitrogen.

The reaction product III is isolated after a sequence of adding 1 to 5 equivalents of a weak base whose basicity lies in the range of pH=8-10 such as sodium or potassium bicarbonate followed by temperature equilibration to 0° to 20° C. and then by conventional techniques in the art including washing, crystallization and/or chromatography. Yields of purified product III are in the range of 40 to 80%.

Following formation of the desired carbapenems of general formula III, the carboxyl protecting group $R^5$ of these intermediates may be optionally removed by conventional procedures such as solvolysis, chemical reduction or hydrogenation. Where a protecting group such as p-nitrobenzyl, benzyl or benzhydryl is used, it can be removed by catalytic hydrogenation, intermediates III in a suitable solvent such as dioxane-water-ethanol, tetrahydrofuran-diethylether-buffer, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature from 20° to 40° C. or from about 0.2 to 4 hours. Protecting groups such as 2,2,2-trichloroethyl may be removed by mild zinc reduction. The allyl protecting group may be removed by using a catalyst comprising a mixture of a palladium compound and triphenylphosphine in a suitable aprotic solvent such as tetrahydrofuran, methylene chloride or diethyl ether. Similarly, other conventional carboxyl protecting groups may be removed by methods known to those skilled in the art.

Thus, in Step 6, carbapenem esters of general formula III are deblocked according to the nature and chemical reactivity of their ester to form the carbapenem of general formula XI where $R^2$ and $R^3$ are hereinabove defined. The method of product isolation in Step 6 will vary on the method of deblocking used. But all methods used in this transformation follow conventional techniques in the art including chromatography and lypophilization.

It is usual to isolate carbapenem XI as an alkali metal salt wherein $R^{15}$ is a lithium, sodium or a potassium ion or as a water soluble zwitterinic specie, whereby $R^{15}$ represents the anionic component an internal salt pair, dependant on the nature of the $R^3$ substituent.

Compounds of Formula III where $R^5$ is a physiologically hydrolyzable ester such as acetoxymethyl, pivaloyloxymethyl, methoxymethyl, etc., may be administered directly to the host without deblocking since such esters are hydrolyzed in vivo under physiological conditions.

A variation of Scheme I allows other methods to prepare ketoester IX and these preparations follow in Scheme 2.

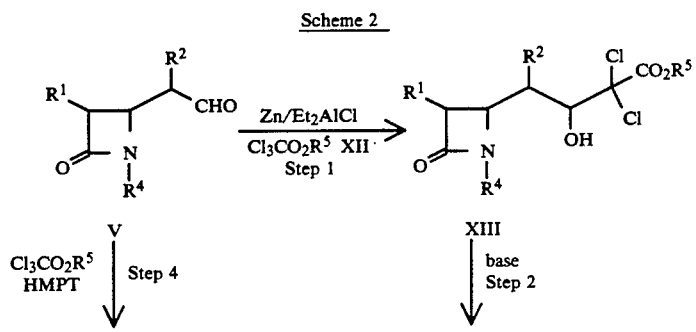

Scheme 2

Scheme 2

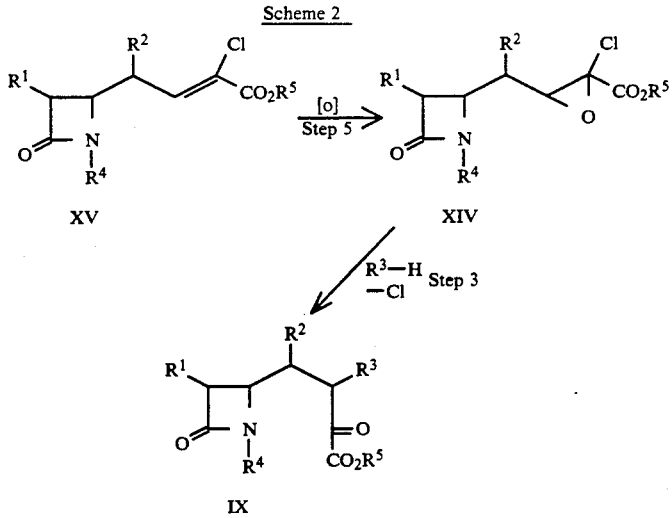

In Step 1 of Scheme 2, hexamethylphosphorus triamide mediated condensation of the azetidinone aldehyde V and the trichloroacetic acid ester of formula XII, where $R^5$ is hereinabove defined, produces the hydroxydichloroester of formula XIII, wherein $R^1$, $R^2$, $R^4$ and $R^5$ are hereinabove defined. The reaction conditions that are utilized in this step are similar to those in similar transformations found in J. Villieras et al., *Bull. Chem. Soc. France*, pp. 898 (1971).

In Step 2 of Scheme 2, the α-chloro-α,β-epoxyester of formula XIV, wherein $R^1$, $R^2$, $R^4$ and $R^5$ are hereinabove defined, is formed by contacting the hydroxydichloroester of formula XIII with a suitable base in a suitable solvent. Bases that are suited for α-chloro-α,β-epoxyester XIV formation include, but are not limited to, lithium, sodium or potassium bis(trimethylsilylamide), sodium hydride, lithium diisoprpylamide, lithium piperidide and potassium tert-butoxide and suitable solvents include tetrahydrofuran, dimethoxyethane, diethyl ether, dimethylformamide, acetonitrile, toluene and methylene chloride. An excess of base is preferred relative to XIII generally in the ratio of 1.1–2.0 to 1 respectively. Reaction concentrations usually are maintained in the range of 0.2 to 1.0 molar for the limiting reactant XIII. Conversion of XIII to XIV proceeds in a temperature range of −20° to 20° C. and contact times of base with XIII usually on the order of 0.1 hour to 12.0 hours depending on the base employed.

The reaction product XIV is isolated after a sequence which initially involves quenching the reaction with a slight excess of a weak acid such as acetic acid or potassium dihydrogen phosphate as a 1 M aqueous solution, followed by conventional techniques in the art including filtration, washing, crystallization, chromatography and the like.

In Step 3 of Scheme 2, the α-chloro-α,β-epoxyester of formula XIV is opened by the nucleophilic conjugate base of the specie $R^3$—H, wherein $R^3$ is hereinabove defined, in a suitable solvent and temperature range. The conjugate base of specie $R^3$—H is formed by treating $R^3$—H in a suitable anhydrous solvent such as tetrahydrofuran, dimethoxyethane, diethyl ether, acetonitrile, toluene, dioxane or dimethylformamide with a suitable base, such as, but not limited to, lithium, sodium or potassium bis(trimethylsilyl)amide, sodium hydride, sodium hydroxide, potassium tert-butoxide, triethylamine, diisopropyl ethylamine, 1,8-diazabicyclo[5.4.0]undec-7-ene (DBU), alkyl lithiums such as methyl-n-butyl- or sec-butyllithium, methylmagnesium bromide or ethyl magnesium bromide. Suitable temperatures for forming the conjugate base are in the range from −70° to 20° C. depdending on the specie $R^3$—H.

The α-chloro-α,β-epoxyester XIV is then contacted with the conjugate base of the specie $R^3$—H. The above process in Step 3 may be performed sequentially or in situ wherein a suitable base is contacted with the pair $R^3$—H and α-chloro-α,β-epoxy-ester XIV. Anther alternative that can be employed equally well is to preform the conjugate base of species $R^3$—H as described above then isolate and purify this conjugate base using conventional techniques in the art. One advantage in pre-forming and isolating conjugate base before contacting it with the α-chloro-α,β-epoxyester XIV in Step 3 is the realization of less unwanted side products in the product isolation and purification stage.

In Step 3 of Scheme 2, an excess of conjugate base of species $R^3$—H relative to XIV is used and generally is preferred in the range of 1.1–2.0 to 1. Reaction concentrations usually are maintained in the range of 0.2 to 1.0 molar for the limiting reagent, XIV. Reaction temperatures usually are in the range of −20° to 50° C. depending on the nucleophilicity of the conjugate base of species $R^3$—H. Reactions of this type are best performed under an inert atmosphere of nitrogen or argon.

The product IX of Step 3 in Scheme 2 is isolated in similar fashion as noted for the synthesis of IX in Scheme 1.

Another alternate synthesis of XIV is described beginning with Step 4 of Scheme 2. Using the procedure disclosed in K. Takai et al., *Bull. Chem. Soc. Japan*, vol. 53, pp. 1698 (1980) the aldehyde is contacted with the trichloroacetic acid ester XII in the presence of zinc and diethylaluminum chloride in tetrahydrofuran solvent to form the α-chloroacrylate ester XV, wherein $R^1$, $R^2$, $R^4$ and $R^5$ are hereinabove described. Yields for this process range from 40 to 85% depending on the nature of $R^2$, $R^4$ and $R^5$ and product isolation and purification following conventional techniques in the art including dilution, washing, chromatography and/or crystallization.

In Step 5 of Scheme 2, the α-chloro-acrylate ester XV is epoxidized to the α-chloro-α,β-epoxyester XIV.

A number of applicable epoxidizing reagents and reaction conditions are useful here. The method of W. Adam et al. *Tetrahedron Letters*, vol. 31, pp. 331-4 (1990) utilizes dimethyldioxirane to epoxidize electron deficient double bond similar to that in Compound XV. Additionally, the method of M. Ashwell et al., *Tetrahedron*, vol. 46, no. 21, pp. 7429-7442 (1990) is effective in converting electron poor double bonds such as that in XV to XIV. Product isolation and purification follow conventional techniques and yields of product XIV vary with the nature of $R^2$, $R^4$ and $R^5$ but usually are in the range of 45-85%.

In Scheme 3, a novel strategy is disclosed for the synthesis of alkylsubstituted α-ketoesters of general formula XXII which cyclize to 2-alkylsubstituted carbapenems of general formula XXIII.

resented in formula XVIII. The rational for the use of either Wittig reagent XVI or XVII and the generalized method is covered in H. O. House in "Modern Synthetic Reactions" W. A. Benjamin, Inc., Menlo Park, Calif. 1972, pp. 682-709.

Another method to prepare the olefin adduct XVIII that is not shown in Scheme 3 is via a base catalyzed reaction of the aldehyde V with a dichloroacetate of formula $CHCl_2CO_2R^5$ wherein $R^5$ is hereinabove defined. The method of A. Takeda et al., *Bull. Chem. Soc. Japan*, vol. 43, 2997 (1977) is followed here.

In formulae XVI-XVIII, $R^1$, $R^2$, $R^4$ and $R^{11}$ are hereinabove defined. $R^{16}$ is any suitable electron withdrawing group such as, but not limited to, $-CO_2R^5$, $-C(R^h)=NR^i$, $-C(O)R^a$, $-C(S)R^a$, $-C(O)NR^hR^i$, $-C(S)NR^hR^i$, $-F$, $-Cl$, $-Br$, $-CF_3$, $-CCl_3$,

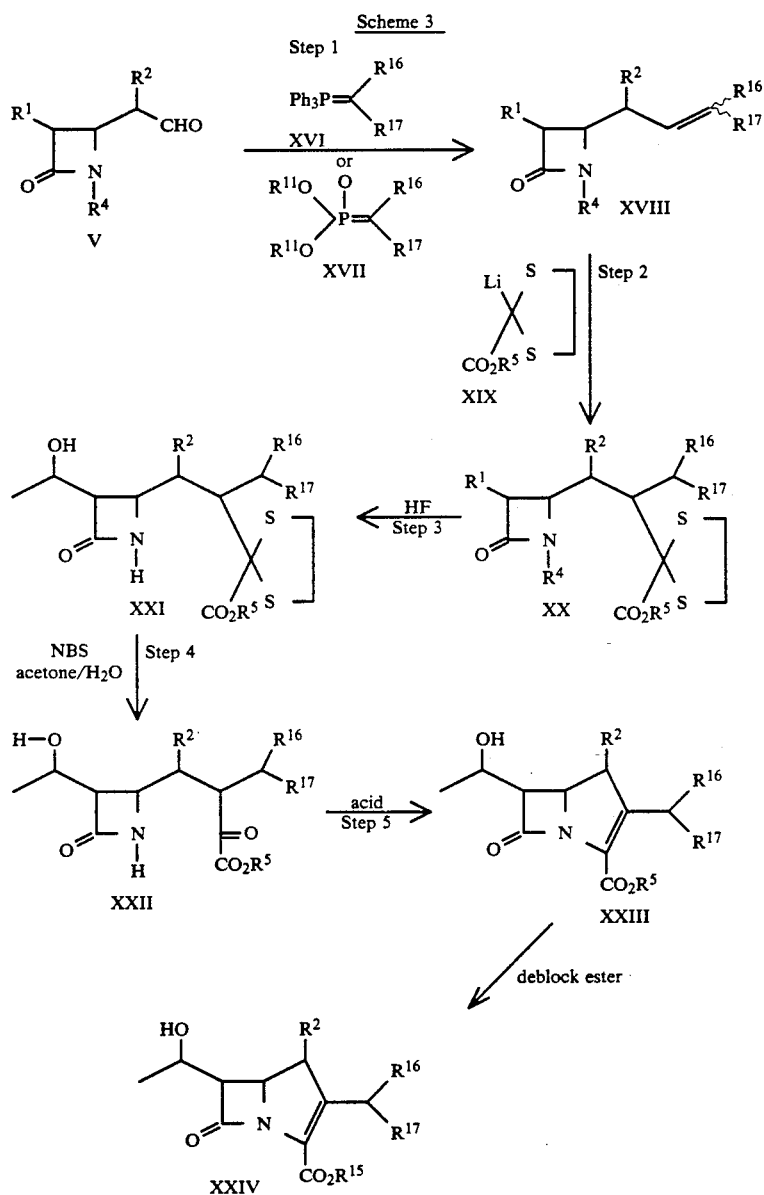

In Step 1 of Scheme 3, the aldehyde V is contacted with a suitable Wittig reagent XVI or XVII to form the olefin adduct XVIII. The Wittig methodology utilized in this step is a common technique for the conversion of an aldehyde functionality to the olefinic adduct as rep- $-SO_2R^a$, $-SOR^a$, $-P(O)(OR^i)(OR^h)$, $-P(O)(NR^iR^h)_2$, $-NO_2$, $-CN$, $-NC$, $-SO_2NR^hR^i$ wherein $R^5$, $R^h$, $R^i$ and $R^a$ are hereinabove defined;

$R^{17}$ is hydrogen, substituted silylgroups such as trimethylsilyl, triethylsilyl, tert-butyldimethylsilyl, substituted or unsubstituted alkyl groups which may be branched or straight chain having 1-5 carbon atoms such as methyl, ethyl, n-propyl, iso-propyl, n-butyl; phenyl-substituted alkyl groups such as benzyl, phenyl, any of such alkyl and phenyl groups being optionally substituted by amino,($C_1$-$C_4$) alkylamino, hydroxy, ($C_1$-$C_3$) alkoxy, mercapto, ($C_1$-$C_3$) alkylthio, sulphamoyl, carbamoyl, nitro, fluoro, chloro, bromo, carboxy and salts and esters thereof; or any suitable electron withdrawing group as stated for $R^{16}$.

Other alternatives to the Wittig methodology exist which can be utilized with equal success in the conversion of aldehyde V to olefin XVIII in Step 1. The Knoevenagel reaction can be employed for substrates of the conjugate base form of the compound of general formula $R^{16}$—$CHR^k$—$R^{17}$ where $R^k$ is hereinabove defined and $R^{16}$ and $R^{17}$, generally in these applications, are both electron withdrawing functionalities. The methods reviewed by Jones in *Organic Reactions*, vol. 15, pp. 204–599 (1967) generally are illustrative of the hereinabove described transformation.

In compound XVIII the double bond geometry can be either E or Z.

In Step 2 of Scheme 3, the lithio adduct XIX where $R^5$ is hereinabove defined is contacted with XVIII to form the 1,4-addition product XX. The use of lithio adduct XIX in conjugate 1,4-additions in similar systems is common in the art and a representative example is disclosed in J. L. Herrmann et al., *Tetrahedron Letters*, no. 28, pp. 2599–2602 (1973). Product isolation and purification in Step 2 utilizes common techniques as in the cited disclosure and product yields range from 60 to 95% depending on the nature of $R^{16}$ and $R^{17}$.

In Step 3 of Scheme 3, the tert-butyldimethylsilyl group of $R^4$ in dithioketal XX is hydroxyled to the corresponding N-H functionality via standard procedures in the art that entails contacting XX with tetra-n-butylammonium fluoride in acetic acid-tetrahydrofuran solvent. According to the method of Guthikonda et al., *J. Med. Chem.*, Vol. 30, pp. 871–880 (1987). Product isolation and purification follows the cited disclosure and product yields are in the range of 70 to 95%. Another method for converting XX to XXI are hereinabove discussed in Scheme 1/Step 4.

In Step 4 of Scheme 3, the dithioketal of compound XXI is hydrolyzed to XXII using n-bromosuccinimide (NBS) in acetone/water solvent system. This type of hydrolysis is common in the art and the procedure of E. J. Corey et al., *J. Org. Chem.*, vol. 36, no. 23, pp. 3553–60 (1971) is exemplary. Product isolation and purification follow standard techniques and yields of product XXII are in the range of 80–90%.

In Step 5 of Scheme 3, the α-ketoester XXII is contacted with a suitable acid in a suitable solvent and temperature range to cyclize and form the carbapenem product XXIII, where $R^2$, $R^5$, $R^{16}$, $R^{17}$ and acid are hereinabove described. The process in Step 5 is similar in all parameters as that disclosed in Step 5 of Scheme 1.

In Step 6 carbapenem esters of general formula XXIII are deblocked according to the nature and chemical reactivity of their ester group to form the carbapenem of general formula XXIV where $R^2$, $R^{15}$—$R^{17}$ are hereinabove defined. The method of product isolation will vary on the method of deblocking used. But all methods used in this transformation follow conventional techniques in the art including chromatography and lypophilization.

It is usual to isolate carbapenem XXIV as an alkali metal salt wherein $R^{15}$ is a lithium, sodium or a potassium ion.

Another strategy to prepare 4-alkylazetidinones of general formula I that varies from those shown in Schemes 1, 2 and 3 is shown in Scheme 4.

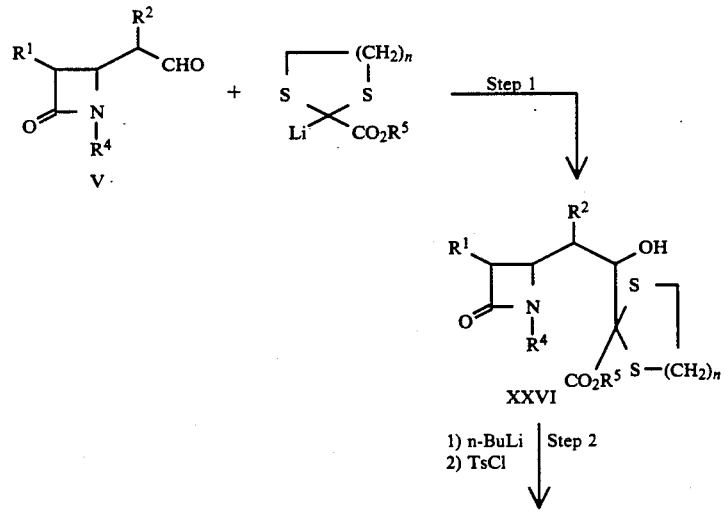

Scheme 4

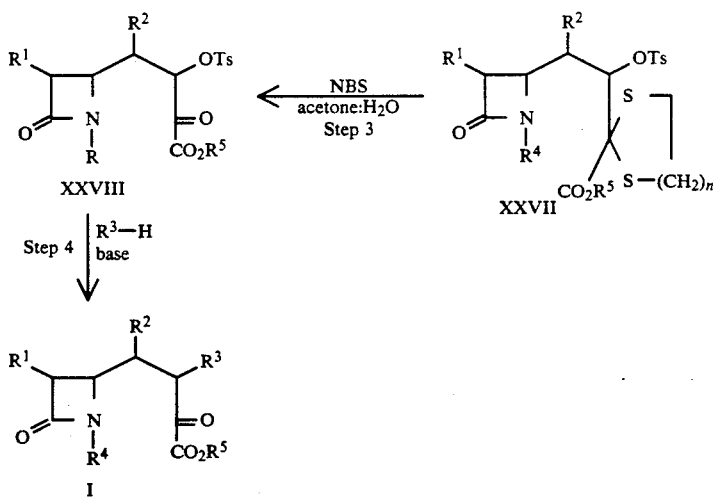

In Step 1 of Scheme 4, the aldehyde of general formula V is contacted with an alkali metal salt of the corresponding dithioketal ester XXV to form, after a mild acid quench, the hydroxy adduct XXVI where $R^1$, $R^2$, $R^4$, $R^5$ are hereinabove defined and n=1 or 2. The actual transformation is representative of an aldol condensation which is common in the art. Both diastereomers of hydroxydithioketal product XXVI are isolated according to conventional techniques. Yield of product XXVI usually range from 50-85% depending on the nature of $R^2$, $R^5$ and the value of n.

In Step 2 of Scheme 4, the hydroxy group of compound XXVI is functionalized to a corresponding leaving group such as its toluenesulfonate (OTS) as shown in compound XXVII where $R^1$, $R^2$, $R^4$, $R^5$ and n are hereinabove defined. Contacting hydroxy compound XXVI in a suitable solvent such as tetrahydrofuran, dioxane, methylene chloride or diethylether in a temperature range of −70° to 20° preferably −20° to 0° C. with a suitable strong base such as, but not limited to, n-butyllithium or methyllithium under an inert solvent such as argon followed by contacting this intermediate alkoxide with toluenesulfonyl chloride (TsCl) produces the derivitized tosylate XXVII. Yields of product XXVII range from 40-90% depending on the nature of $R^2$, $R^5$ and the value of n.

In Step 3 of Scheme 4, the dithioketal functionality of compound XXVII is hydrolyzed using n-bromosuccinimide/acetone/$H_2O$ system to form the ketoester XXVIII, where $R^1$, $R^2$, $R^4$, $R^5$ are hereinabove deester fined. The overall transformation in Step 3 of Scheme 4 is similar in nature to that described in Step 4 of Scheme 3. In the present transformation, yields of product XXVIII vary from 55% to 90%.

In Step 4 of Scheme 4, the tosylate leaving group is displaced with a suitable nucleophilic conjugate base of the specie $R^3$—H to form the ketoester of general formula I where $R^1$—$R^5$ are hereinabove defined. The overall transformation presented in Step 4 of Scheme 4 is similar in all aspects to that described in detail in Step 3 of Scheme 1. Yields of product of general formula I range from 20-90% depending primarily on the nature of the nucleophilic conjugate base of specie $R^3$—H.

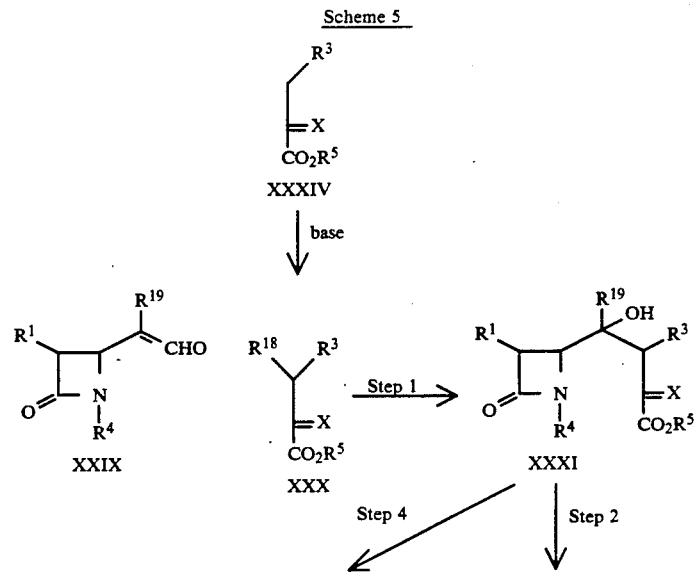

Scheme 5

Scheme 5

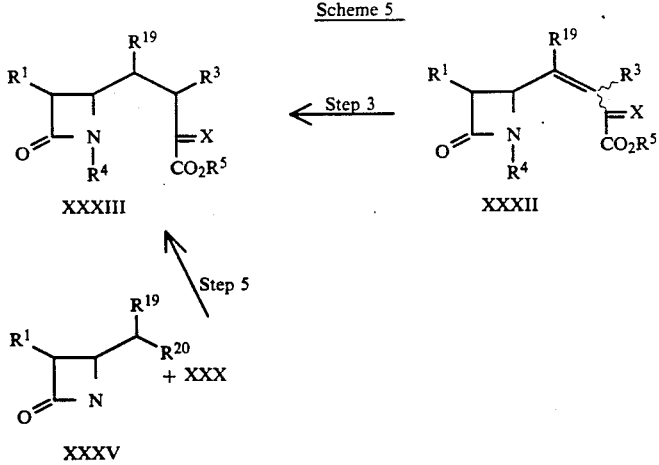

In Scheme 5 a convergent approach to compound of formula XXXIII is presented where $R^1$, $R^3$, $R^4$, $R^5$ and X are hereinabove defined and $R^{19}$ is H or $CH_3$. Compound XXXIII is similar to compound of general formula I and differs only in the more specific definition of $R^{19}$ compared to that of $R^2$ in formula I.

In Step 1 of Scheme 5, the carbonyl substituted azetidinone of formula XXIX is contacted with the ester-alkali metal conjugate base XXX in a suitable solvent such as tetrahydrofuran, dimethoxyethane, diethyl ether, toluene, dioxane dimethylformamide on acetonitrile where $R^{18}$ is lithium, sodium, potassium or magnesium. The conjugate base XXX is formed by contacting the ester of formula XXXIV with a suitable base such as lithium, sodium or potassium bis(trimethylsilyl)amide, lithium diisopropylamide, sodium or potassium hydride; alkyllithiums such as methyllithium, n-butyllithium, sec-butyllithium; alkylmagnesium halides such as methyl magnesium bromide and ethylmagnesium bromide; sodium methoxide, potassium tert-butoxide. Amounts of the base required may vary relative to compound XXXIV depending on the nature of X. Preferred is where X=N—OH and therefore two equivalents of base relative to XXXIV are required. The generation of conjugate base XXX is done in a suitable anhydrous solvent such as tetrahydrofuran, diethylether or dimethylformamide at a temperature ranging from −70° to 0° under an inert atmosphere such as argon.

An excess of reagent XXX relative to the azetidinone XXIX generally is preferred in the ratio range of 1.0–3.0 to 1. Reaction concentrations usually are maintained in the range of 0.2 to 1.5 molar for the limiting reagent XXIX and the overall contact time between reagents XXIX and XXX varies but usually ranges from 0.25 to 4 hours. The reaction product XXXI is isolated by conventional techniques in the art including dilute acid neutralization, dilution, aqueous washing chromatography and/or crystallization.

In Step 2 of Scheme 5, the hydroxy compound of formula XXXI is dehydrated to the olefin of formula XXXII where $R^1$, $R^3$—$R^5$, $R^{19}$ and X are hereinabove defined. The dehydration is best conducted in a suitable solvent such as tetrahydrofuran, dimethoxyethane, acetonitrile, methylene chloride or dimethylformamide utilizing reaction temperatures in the range of −30° to 50° C.. Secondary ($R^{19}$=H) and tertiary alcohols ($R^{19}$=$CH_3$) such as what is represented in general formula XXXI dehydrate in the presence of various acids such as phosphorous pentoxide, zinc chloride, magnesium iodide, boron trifluoride etherate or aqueous mineral acid. This technique is a commonly practiced one in the art and a more comprehensive treatment of this topic is found in J. March in "Advanced Organic Chemistry" John Wiley and Sons, New York 1985, pp. 901–906.

Product XXXII isolation and purification entails conventional techniques such as contacting the product with aqueous mineral acid to ensure the hydrolysis of the oxime (X=NOH) to the corresponding α-ketoester functionality present in the product XXXII, dilution with an organic solvent such as ethyl acetate, water washing and chromatography and/or crystallization. The product XXXII is isolated as a mixture of E and Z geometric isomers whose ratio is dependent on the acid employed in the dehydration step as well as $R^{19}$ and $R^3$.

In Step 3 of Scheme 5 the conjugated double bond of XXXII is reduced using suitable reaction conditions. The saturated alkyl azetidinone product XXXIII can be a mixture of all possible diastereomers on the carbons bearing $R^{19}$ and $R^3$ where $R^1$, $R^3$, $R^5$ and $R^{19}$ are hereinabove defined. A number of suitable reaction conditions are known in the art to reduce α,β-unsaturated carbonyl compounds such as XXXII. The example of T. Tsuda et al., J. Org. Chem., Vol. 51, pp. 537–540 (1986) employs a diisobutylaluminum hydride-method that is dependent on a methylcopper (I) catalyst in the presence of hexamethylphosphorus triamide. Another useful method is that of Y. D. Vankar et al., Synth. Commun., Vol. 17, no. 2, pp. 181–187 (1987) which uses sodium iodide/trimethylsilyl chloride combination for this transformation in Step 3. Product isolation by the above cited methods entails conventional techniques such as quenching with mild acid, dilution, washing with water, chromatography and/or crystallization.

Another useful method to prepare the α-ketoester of general formula XXXIII in Scheme 5 is shown in Step 4. In this sequence, the alcohol of XXXI is reduced directly to form XXXIII. The method of reducing secondary alcohols ($R^{19}$=H in XXXI) and tertiary alcohols ($R^{19}$=H in XXXI) is a common technique in the art. An exemplary method to reduce secondary alcohols is found in D. H. R. Barton et al., J. Chem. Soc. Perkin Trans. I, pp. 1574–78 (1975). Tertiary alcohols, on the other hand, require slightly different conditions (oxalyl chloride, N-hydroxypiperidine-2-thione in the presence of a catalytic amount of tert-butylthiol) and the method of D. H. R. Barton et al., *J. Chem. Soc., Chem. Commun.*, pp. 774-5 (1984) serves as an adequate example of the direct reduction of XXXI to XXXIII where in this case $R^{19}=CH_3$ is preferable. Product isolation follows conventional techniques.

The most direct method to prepare the α-ketoester of general formula XXXIII is shown in Step 5 of Scheme 5. In this one-step procedure, the azetidinone of general formula XXXV is contacted with the ester-alkali metal conjugate base XXX, hereinabove described, in a suitable solvent and temperature range to form the product XXXIII, where $R^1$, $R^3$—$R^5$, $R^{19}$ and X are hereinabove defined and $R^{20}$ is any suitable leaving group, such as, but not limited to, I, Br, $OSO_2CH_3$, $OSO_2$-4-methylphenyl, $OCOCH_3$, $OCOCF_3$, $OP(O)(OPh)_2$. An excess of reagent XXX relative to the azetidinone XXXV is preferred in the ratio range of 1.0-5.0 to 1. Reaction concentrations usually are maintained in the range of 0.2 to 3 molar for the limiting reagent XXXV and the overall contact time between reagents XXXV and XXX varies between 0.25 to 4 hours. Suitable solvents for this displacement reaction in Step 5 are tetrahydrofuran, dimethoxyethane, dioxane, dimethylformamide and dimethylsulfoxide. Reaction temperatures can range from −30° to 50° C.. The product XXXIII is isolated and purified by conventional procedures that include quenching the reaction with mild aqueous and allowing sufficient contact time between acid and crude reaction mixtures to allow hydrolysis of the oxime to the α-ketoester of product XXXIII, dilution with an organic solvent such as ethylacetate, washing with water, chromatography and/or crystallization.

In formula XXXIII, $R^1$ and $R^4$ are independently selected from the list shown above. Preferred are where $R^1$ is 1-(tert-butyldimethyl)siloxyethyl and $R^4$ is tert-butyldimethylsilyl. Removal of these types of protecting groups may be achieved by any number of conventional techniques but most efficiently with hydrogen fluoride in acetonitrile-water solvent according to the generalized procedure of R. Newton et al., *Tetrahedron Letters*, no. 41, pp. 3981-3982 (1979).

In a manner that is similar to that described in Scheme 1, Step 5, the α-ketoester XXXIII is cyclized to the carbapenem product where $R^2$ is equal to $R^{19}$ as hereinabove defined. Product isolation and purification follow conventional techniques described for Step 5, Scheme 1.

In Scheme 6, a method to prepare carbacephems of general formula XLIV is presented. In Step 1 of Scheme 6, the aldehyde of general formula V is contacted with the ylid methoxymethylenetriphenyl phosphorane in tetrahydrofuran solvent at 0° C. to form both geometric isomers of the product XXXVIII by conventional techniques in the art. The vinyl ether XXXVIII is hydrolyzed in Step 2 of Scheme 6 with dilute mineral acid to the corresponding aldehyde XXXIX in tetrahydrofuran solvent at 25° C., where $R^1$, $R^2$ and $R^4$ are hereinabove defined. This method for one carbon chain homologation is a commonly used technique similar to that disclosed in *J. Org. Chem.*, Vol. 40, p. 1989 (1975).

Scheme 6

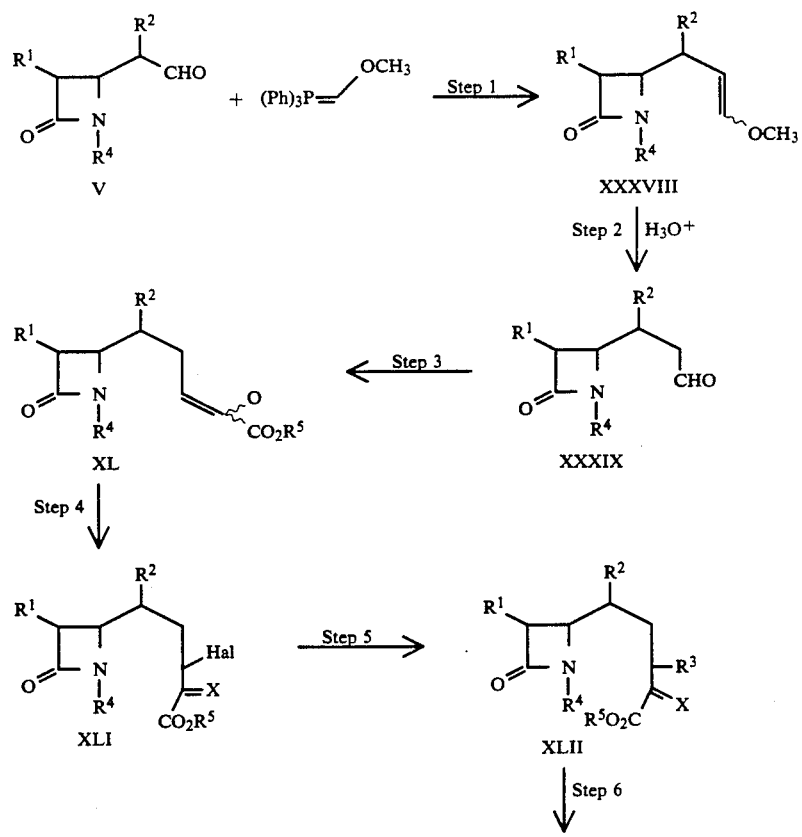

Scheme 6

-continued

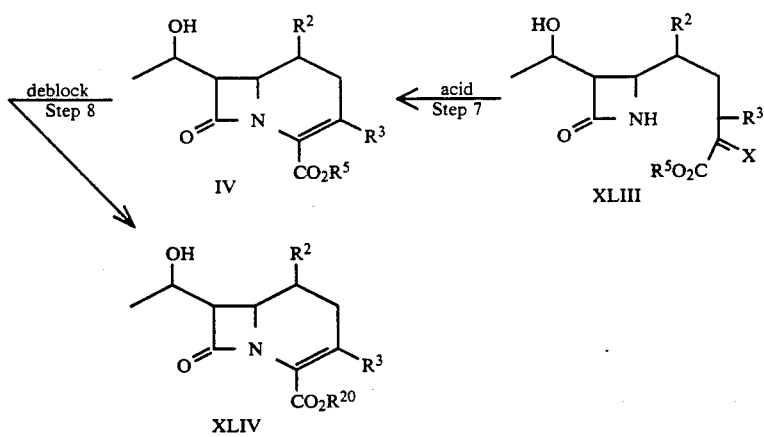

The remainder of the steps in Scheme 6, starting with aldehyde XXXIX, i.e., Steps 3-8 are analogous in all experimental parameters, isolation and purification conditions as was disclosed in Steps 1-6 respectively in Scheme 1, where the definitions of all variables $R^1$-$R^{20}$, X, acid etc., are hereinabove defined.

It will be appreciated that certain products within the scope of Formulae II and IV

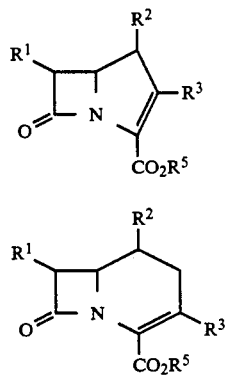

may be formed as optical isomers as well as epimeric mixtures thereof. It is intended that the present invention include within its scope all such optical isomers and epimeric mixtures. For example, when the 6-substituent in II and IV are 1-(t-butyldimethyl)siloxyethyl, such substituent may be either R or S configuration with the R configuration being preferred. Likewise, the configuration of the carbapenem nucleus may be 5R or 5S and 6R or 6S with 5R, 6S being the preferred configuration.

In the foregoing word description of the above schematic reaction diagrams for the synthesis of carbapenem and carbacephem antibacterials, it is understood that there is latitude in selection of precise reaction parameters. Suggestion of this latitude and its breadth is generally indicated by the enumeration of equivalent solvent systems, temperature ranges, protecting groups, and range of identities of involved reagents.

The compounds of this invention and their preparation can be understood further by the following examples, but should not constitute a limitation thereof.

EXAMPLE 1

1,3-Dithiolane-2-propanoic acid, β-[[1-[(1,1-dimethylethyl)dimethylsilyl]-3-[1-[[(1,1-dimethylethyl)dimethylsilyl]oxy]ethyl]-4-oxo-2-azetidinyl]methyl ]methyl ester, [2R-[2α(R* and S*), 3β(R*)]]-

Benzyl 1,3-dithiolane-2-carboxylate (Gazz. Chim. Ital., 120(3), 165-70, 1990), 682 mg, is dissolved in 9.3 ml of tetrahydrofuran and cooled to −78° C. under an argon atmosphere. To the cooled mixture is added dropwise lithium bis(trimethylsilyl) amide (3.1 mls of a 1 M solution in tetrahydrofuran). After stirring at −78° C. for 30 minutes 2-butenoic acid, 4-[1-[(1,1-dimethylethyl)dimethylsilyl]-3-[1-[[(1,1-dimethylethyl)dimethylsilyl]oxy]ethyl]-4-oxo-2-azetidinyl]-,methyl ester, [2R-[2α(E),3β(R*)]] (1.14 g) is added dropwise as a solution in 4.6 ml tetrahydrofuran. After 1 hour, the reaction is quenched by adding 5 ml 10% acetic acid and diluting with ethyl acetate. After partitioning, the organic layer is washed twice with water and once with brine. After drying over anhydrous magnesium sulfate and filtration, the resulting solution is concentrated and the crude oil flash chromatographed on silica gel with 15% ethyl acetate in hexanes. The compound is obtained as a mixture of diastereomers (1.4 g, 80%). The product has also been prepared as disclosed in Tetrahedron Lett., vol. 24, pp. 3251-4 (1983).

$^1$H NMR (CDCl$_3$) Major Isomer: δ7.33(br s,5H), 5.18(ABq, 2H), 4.1(m,1H), 3.65(s,3H), 3.52(m,1H), 3.4-3.2(m,4H), 2.9(m,1H), 2.8-2.7(m,2H), 2.33(dd,1H), 1.84(br t,1H), 1.48(t,1H), 1.1(d,3H), 0.92(s,9H), 0.85(s,9H), 0.2-0(4s,3H each). Minor Isomer: δ7.32(br s,5H), 5.22(d,1H), 5.1(d,1H), 4.15(m,1H), 3.9(m,1H), 3.6(s,3H), 3.4-3.2(m,4H), 3.0-2.9(m,2H), 2.5(dd,1H), 2.35(dd,1H), 2.21(m,1H), 1.38(m,1H), 1.19(d,3H), 0.9(s,9H), 0.85(s,9H), 0.2-0(4s,3H each).

EXAMPLE 2

2-Azetidinebutanoic acid, 3-[1-[[(1,1-dimethylethyl)dimethylsilyl])-dimethylsilyl]oxy]ethyl]-4-oxo-β-[2-[phenylmethoxy)carbonyl]-1,3-dithiolan-2-yl)-methyl ester, [2R-[2α(R* and S*), 3β(R*)]]-

The compound prepared in Example 1 (504 mg) in 8.3 ml dichloromethane is cooled in an ice bath and treated with glacial acetic acid (0.064 ml) and then tetrabutylammonium fluoride (1.1 ml of a 1 M solution in tetrahydrofuran). After stirring for 10 minutes, the cooling bath is removed and the mixture is stirred for an additional 20 minutes. The reaction is then diluted with diethyl ether and then washed twice with saturated sodium bicarbonate solution. After washing once with brine, the organics are dried over anhydrous magnesium sulfate, filtered and concentrated in vacuo. The resulting oil is then flash chromatographed on silica gel using 30% ethyl acetate in hexanes. Both diastereomers are separated.

Minor Isomer: 95.8 mg; Major Isomer: 271 mg; Total Yield: 366.8 mg (87%).

$^1$H NMR (CDCl$_3$) δMajor Isomer: 7.35(br m,sH), 5.95(br s,1H), 5.20(s,2H), 4.12(m,1H), 3.67(s/m,4H), 3.4–3.2(m,4H), 3.0(m,1H), 2.83(dd,1H), 2.65(m,1H), 2.35(dd,1H), 1.9(m,1H), 1.6(m,1H), 1.15(d,3H), 0.85(s,9H), 0.05(s,6H).

EXAMPLE 3

Pentanedioic acid,
3-[[3-1-[[(1,1-dimethylethyl)dimethylsilyl)-dimethylsilyl]oxy-]ethyl]-4-oxo-2-azetidinyl]methyl]-[2R-2α(R* and S*), 3(3(R*)]]-

N-Bromosuccinimide (748 mg) is dissolved in 10 ml of 97:3 acetone:H$_2$O and cooled to −10° C. To this cold mixture is added the dithiolane described in Example 2 (298 mg) in 10 ml acetone (addition over 5 minutes). The bath temperature is subsequently allowed to warm to 10° C. and stirred at this temperature for 30 minutes. The reaction is then quenched with 10% sodium thiosulfate solution and stirred until decolorized. The mixture is diluted with ethyl acetate and partitioned. The organic layer is washed once with 1M sodium bicarbonate solution, once with brine, and dried over anhydrous magnesium sulfate. The crude α-keto ester is purified via flash chromatography with 30% ethyl acetate in hexanes to afford 150 mg (58%) as a colorless oil.

$^1$H NMR (CDCl$_3$) δ7.35(m,5H), 5.95(br s,1H), 5.35(d,minor isomer), 5.30(s,2H), 5.14(d,minor isomer), 4.1(m,1H), 3.75(m,1H), 3.63(s,minor isomer), 3.6(s,3H), 3.57(m,1H), 2.88(dd,1H), 2.75(m,1H), 2.55(dd,1H), 2.05(m,1H), 1.76(m,1H), 1.15(d,3H), 0.86(s,minor isomer), 0.84(s,9H), 0.05–0(3s,6H).

EXAMPLE 4

1-Azabicyclo[3.2.0]hept-2-ene-3-acetic acid,
6-[1-[[(1,1-dimethylethyl)dimethylsilyl]oxy]ethyl]-7-oxo-2-[(phenylmethoxy)carbonyl]-, methyl ester,
[5R-[5α,6β(R*)]]-

Concentrated hydrochloric acid (0.350 ml, 37%) is added to 4 ml dichloromethane. This mixture is stirred rapidly as the o-keto ester described in Example 3 in 2 ml dichloromethane is added. After stirring for 20 minutes, the reaction is diluted with ethyl acetate and quenched with 1 M sodium bicarbonate solution. The organic layer is washed once with brine and dried over anhydrous magnesium sulfate. After filtration and concentration, the residue is purified via flash chromatography with 20% ethyl acetate in hexanes. The pure carbapenem obtained amounts to 78.4 mg (35%). IR(cm$^{-1}$) 1780

$^1$H NMR (CDCl$_3$) δ7.46–7.25(m,5H), 5.26(ABq,2H), 4.2(m,2H), 3.85(d,1H), 3.7(s,3H), 3.6(d,1H), 3.15(m,1H), 2.95(m,1H), 1.15(d,3H), 0.96(s,9H), 0.09(s,6H).

EXAMPLE 5

Propanedioic acid,
[2-[1-[(1,1-dimethylethyl)dimethylsilylsilyl]-3-[1-[[(1,1-dimethylethyl)dimethylsilylsilyl]oxy]ethyl[-4-oxo-2-azetidinyl]ethylidene]-, dimethyl ester, [2R-2α, 3β(R*)]]-

The title compound was prepared using the method described by W. Lehnert, *Tetrahedron Letters*, No. 54, p. 4723–4724, 1970. Titanium tetrachloride solution (52 ml of a 1 M solution in methylene chloride) is added to 100 ml of ice cold dry tetrahydrofuran under argon. To the resulting bright yellow slurry is added dropwise a mixture of 2-azetidineacetaldehyde, 3-[1-[[(1,1-dimethylethyl)dimethylsilyl]oxy]ethyl]-4-oxo-1-(triethylsilyl)-[2R-[2α,3β(R*)]]- (10 g) (prepared as described in EP 37081A1) and dimethylmalonate (3 g) in 35 ml dry THF. When the addition is complete (10 minutes) pyridine (8.4 ml) is added rapidly dropwise. After 20 minutes, the cooling bath is removed and the mixture is stirred for 15 hours. The reaction is diluted with diethyl ether, quenched with water, and partitioned. The organic layer is washed once with water, once with saturated sodium bicarbonate solution and once with brine. The resulting organic layer is dried over anhydrous magnesium sulfate, filtered, and concentrated. The resulting residue is purified via filtration through a plug of silica gel 60 eluting with 20% ethyl acetate in hexanes. The title compound is obtained as tan crystals, 10 g (77%).

$^1$H NMR (CDCl$_3$) δ6.99(t,1H), 4.13(m,1H), 3.84(s,3H), 3.79(s,3H), 3.73(m,1H), 2.87(m,2H), 2.53–2.45(m,1H), 1.16(d,3H), 0.96(s,9H), 0.87(s,9H), 0.24(s,3H), 0.23(s,3H), 0.07(s,3H), 0.04(s,3H).

EXAMPLE 6

Propanedioic acid,
[2-[1-(1,1-dimethylethyl)dimethylsilyl]3-[1-[(1,1-dimethylethyl)dimethylsilyl]oxy]ethyl]4-oxo-2-azetidinyl]-1-[2-[(phenylmethoxy)carbonyl]1,3-dithiolan-2-yl]ethyl]-, dimethyl ester, [2R-[2α(R* and S*), 3β(R*)]]-

Benzyl 1,3-dithiolane-2-carboxylate (106 mg) is dissolved in 1.6 ml dry tetrahydrofuran under argon and cooled to −78° C. To this solution is added lithium bistrimethylsilylamide (0.53 ml of a 1 M solution in tetrahydrofuran). After 30 minutes, the diester prepared in Example 5 (200 mg) in 0.8 ml dry tetrahydrofuran is added dropwise. After the addition is complete, the reaction is stirred for 15 minutes and then quenched with 10% aqueous acetic acid. The mixture is diluted with diethyl ether/water and partitioned. The organic layer is washed once with water, once with brine, and dried over magnesium sulfate. The residue obtained after filtration and concentration is chromatographed on silica gel with 20% ethyl acetate in hexanes. The total amount of title compound obtained amounted to 279 mg (94%). The mixture of diastereomers is partially separated.

$^1$H NMR (CDCl$_3$) Major Isomer: δ7.37(m,5H), 5.21(s,2H), 4.14(m,1H), 3.90(d,1H), 3.73(s,6H), 3.4–3.26(m,6H), 2.93(m,1H), 2.49(m,1H), 1.34(m,1H), 1.19(d,3H), 0.92(s,9H), 0.87(s,9H), 0.23(s,3H), 0.16(s,3H), 0.06(s.3H),, 0.04(s,3H). Minor Isomer: δ7.36(m,5H), 5.31(d,1H), 5.16(d,1H), 4.26(m,1H), 4.04(d,1H), 3.96(br d,1H), 3.71(s,3H), 3.69(s,3H), 3.39–3.24(m,5H), 3.02(m,1H), 2.25(m,1H), 1.97(dd,1H), 1.28(d,3H), 0.95(s,9H), 0.89(s,9H), 0.26(s,3H), 0.16(s,3H), 0.08(s,3H), 0.05(s,3H).

EXAMPLE 7

1,3-Dithiane-2-carboxylic acid, 2-[2-[1-[((1,1-dimethylethyl)dimethylsilyl]3-[1-[[(1,1-dimethylhydroxyethyl], phenylmethyl ester, [2R-[2α(R* or S*), 3β(R*)]]-

Benzyl 1,3-dithiane-2-carboxylate (*J. Org. Chem.*, 452-9, 1978), 1.45 g, in 20 ml dry tetrahydrofuran is cooled to −78° C. under argon and treated dropwise with lithium bistrimethylsilylamide (6.3 ml of 1.0 M solution in tetrahydrofuran). After stirring for 30 minutes at −78° C., the aldehyde (2-azetidineacetaldehyde, 3-[1-[[(1,1-dimethylethyl)dimethylsilyl]oxy]ethyl]-4-oxo-1-(triethylsilyl)-, [2R-[2α,3β(R*)]]-) in 10 ml dry tetrahydrofuran is added dropwise. After the addition, the reaction mixture is stirred for 30 minutes. The reaction is quenched at −78° C. with 10% aqueous acetic acid and allowed to warm to room temperature. The reaction mixture is diluted with ethyl acetate and partitioned. The organic layer is then washed 3 times with water and once with brine. After drying over anhydrous magnesium sulfate and filtration, the solvent is removed in vacuo to give a crystalline slush which is diluted with 10% ethyl acetate in hexanes and chilled in ice. The crystals are collected and rinsed with 10% ethyl in hexanes then hexanes. Drying in vacuo affords 2.04 g (61%) of white crystals. This product corresponds to a single diastereomer of the title compound. M.P. 170°-172° C.

$^1$H NMR (CDCl$_3$) δ7.38(br s,5H), 5.27(s,2H), 4.08-4.02(m,2H), 3.75(br d,1H), 3.16(t,2H), 2.90(d,1H), 2.68(m,3H), 2.02-2.05(m,2H), 1.83(br q,2H), 1.22(d,3H), 0.94(s,9H), 0.89(s,9H), 0.21(s,3H), 0.20(s,3H), 0.08(s,3H), 0.07(s,3H).

EXAMPLE 8

1,3-Dithiane-2-carboxylic acid, 2-[1-(acetyloxy)-2-[1-[(1,1-dimethylethyl)dimethylsilyl]3-[1-[[1,1-dimethylethyl)dimethylsilyl]oxy]ethyl]-4-oxo-2-azetidinylethyl]-, phenylmethyl ester, [2R-[2α, 3β(R*)]]-

The alcohol prepared in Example 7 (0.340 g) is dissolved in 5 ml pyridine and treated with acetic anhydride (1 ml). 4-dimethylaminopyridine (0.05 g) is then added and the reaction is stirred at room temperature for 15 hours. The reaction mixture is diluted with diethyl ether, washed twice with 10% hydrochloric acid and once with brine. The organic layer is dried over anhydrous magnesium sulfate, filtered and concentrated. The resulting residue is chromatographed on silica gel with 20% ethyl acetate in hexanes. The title compound is isolated as a colorless oil 0.348 g (96%).

EXAMPLE 9

2-Azetidinebutanoic acid, β(acetoxy)-1-[(1,1-dimethylethyl)dimethylsilyl]-3-[1-[[(1,1-dimethylethyl)dimethylsilyl]oxy]ethyl]-α,4-dioxo-, phenylmethyl ester, [2R-[2α,3(3(R*)]]-

A solution of N-bromosuccinimide (0.774 g) in 9.8 ml of 97:3 acetone:water is cooled to −10° C. and treated with a solution of the dithiane prepared in Example 8 (0.37 g in 3 ml acetone). The reaction is then allowed to warm to 8° C. over 30 minutes. The reaction is quenched with 10% sodium sulfite and diluted with ethyl acetate. After partitioning, the organic layer is washed once with 1 M sodium bicarbonate and once with brine. After drying over anhydrous magnesium sulfate and filtration, the solvents are removed in vacuo. The resulting residue is chromatographed with 30% ethyl acetate in hexanes and affords 0.227 g (70%) of desired α-keto ester as a colorless oil.

$^1$H NMR (CDCl$_3$) δ7.36(m,5H), 5.4(br d,1H), 5.29(ABq,2H), 5.21(ABq, minor isomer), 4.95(m, minor isomer), 4.29(minor isomer), 4.1(m,1H), 3.74(m,1H), 3.6(m, minor isomer), 2.83(m,1H), 2.7(m, minor isomer), 2.18(m,1H), 2.09(s,3H), 1.94(s, minor isomer), 1.88(m,1H), 1.1(d,3H), 0.9(s,9H), 0.84(s,9H), 0.1-0(4s,3H each).

EXAMPLE 10

1,3-Dithiolane-2-carboxylic acid, 2-[2-[1-[(1,1dimethylethyl)dimethylsilyl]3-[1-[[(1,1-dimethylethyl)dimethylsilyl]oxy]ethyl]-4-oxo-2-azetidinyl]-1-hydroxyethyl]-, phenylmethyl ester, [2R-[2α(R* or S*), 3β(R*)]]-

A solution of benzyl 1,3-dithiolane-2-carboxylate (*Gazz. Chim. Ital.*, 120(3), 165-70, 1990), 1.37 g in 20 ml dry tetrahydrofuran under argon is cooled to −78° C. and treated with a solution of lithium bistrimethylsilyl amide (6.4 ml of 1 M solution in tetrahydrofuran). After 40 minutes, the aldehyde 2-azetidineacetaldehyde, 3-[1-[[(1,1-dimethylethyl)dimethylsilyl]oxy]ethyl]-4-oxo-1-(triethylsilyl)-, [2R-[2α,3β(R*)]]- (2.0 g) in 10 ml of tetrahydrofuran is added rapidly dropwise. After stirring at −78° C. for 35 minutes, the reaction is quenched with 5 ml of 10% acetic acid and the cooling bath is removed. The reaction mixture is diluted with water and ethyl acetate and partitioned. The organic layer is then washed once with brine, dried over anhydrous magnesium sulfate, and filtered. Concentration affords light yellow oily crystals which are slurried in hexanes and cooled in ice. The collected crystals amount to 1.29 g (40%) of the title alcohol as a single diastereomer. MP=133°-136° C.

$^1$H NMR (CDCl$_3$) δ7.35(m,5H), 5.27(ABq,2H), 4.2-3.95(m,2H), 3.77(m,1H), 3.5-3.27(m,4H), 2.94(m,1H), 2.63(dd,1H), 2.08(m,1H), 1.62(t,1H), 1.20(d,3H), 0.93(s,9H), 0.88(s,9H), 0.21(s,3H), 0.20(s,3H), 0.08(s,3H), 0.06(s,3H).

EXAMPLE 11

1,3-Dithiolane-2-carboxylic acid, 2-[2-[1-[(1,1-dimethylethyl)dimethylsilyl]3-[1-[[(1,1-dimethylethyl)dimethylsilyl]oxy]ethyl]-4-oxo-2-azetidinyl]1-[[(4-methylphenyl)sulfonyl]oxy]ethyl-, phenylmethyl ester, 2R-[2α,3β(R*)]]-

The alcohol from Example 10 (1.29 g) is dissolved in 12 ml dry tetrahydrofuran under argon and diluted with 24 ml dry diethyl ether. This mixture is to −78° C. and treated dropwise with n-butylcooled lithium (1.54 ml of 1.6 M solution in hexanes). After several minutes, solid p-toluenesulfonyl chloride (0.433 g) is added in a single portion. The reaction is stirred at −78° C. for 45 minutes then gradually warmed to 0° C. over 30 minutes. The reaction is quenched with water and diluted with ethyl acetate. After partitioning, the organic layer is washed once with water and once with brine. After drying over magnesium sulfate and filtration, the solvents are removed to afford 1.66 g crude tosylate as a faintly yellow oil.

$^1$H NMR (CDCl$_3$) δ7.8(d,2H), 7.37(br s,5H), 7.3(d,2H), 5.26(d,1H), 5.2(d,1H), 5.07(d,1H), 4.24(m,1H), 3.9(m,1H), 3.4-3.15(m,4H), 2.9(m,1H), 2.42(s,3H), 2.33(m,1H), 1.9(m,1H), 1.26(d,3H), 0.91(s,9H), 0.88(s,9H), 0.18(s,3H), 0.10(s,3H), 0.06(s,3H), 0.01(s,3H).

EXAMPLE 12

2-Azetidine butanoic acid. 1-[(1,1-dimethylethyl)-dimethylethyl)dimethylsilyl]-3 -[1-[[(1,1-dimethylethyl)dimethylsilyl]oxy]ethyl]-β-[(4-methylphenyl)sulfonyl]oxy]-α,4-dioxo-, phenylmethyl ester, [2R-[2α,3β(R*)]]-

N-Bromosuccinimide (1.52 g) is dissolved in 19 ml of 97:3 acetone:water and cooled to −5° C. The dithiolane prepared in Example 11 (0.831 g) in 7 ml of acetone is added dropwise over 5 minutes. After the addition, the cooling bath is allowed to warm to 10° C. over 40 minutes. The reaction is quenched at 10° C. with 10% sodium bisulfite and stirred until the orange color is discharged. Dilution with ethyl acetate and water is followed by partitioning. The organic layer is then washed with 1 M sodium bicarbonate and then brine. The residue obtained after drying over magnesium sulfate, filtration and concentration was purified via chromatography on Biosil A. The title compound was obtained as a nearly colorless oil 0.239 g (32%) as a mixture of diastereomers.

$^1$H NMR CDCl$_3$) δ7.78(m,4H), 7.44-7.28(m,14H), 5.47(m,1H), 5.38(d,1H), 5.3(ABq,2H), 5.14(d,1H), 4.88(m,1H), 4.13(m,2H), 3.7(m,2H), 2.85(m,1H), 2.66(m,1H), 2.44(d,6H), 2.3(m,1H), 2.18(m,1H), 2.0-1.8(m,2H), 1,10(d,3H), 1.04(d,3H), 0.9(m,36H), 0.1-0(m,24H).

EXAMPLE 13

2-Azetidinebutanoic acid, 1-(1,1-dimethylethyl)dimethylsilyl]-3-[1-[[(1,1-dimethylethyl)dimethylsilyl]oxy]ethyl]-α,4-dioxo-β-[(phenylmethyl)thio]-, phenylmethyl ester, [2R-[2α(R* and S*), 3β(R*)]]-

A solution of benzyl mercaptan (0.07 ml) in 4.2 ml of dry tetrahydrofuran is cooled to 0° C. under argon. To the ice cold mixture is added sodium bis(trimethylsilyl)amide (0.406 ml of a 1 M solution in tetrahydrofuran). After 15 minutes, the tosylate prepared in Example 12 (0.238 g) in 2.8 ml of dry tetrahydrofuran is added dropwise. After stirring for 20 minutes, the reaction is quenched with water and diluted with ethyl acetate. The organic layer is washed with brine and dried over anhydrous magnesium sulfate. Filtration and concentration affords the crude product as a mixture of diastereomers. Partial separation is achieved via chromatography on silica gel with 20% ethyl acetate in hexanes. The total amount of title compound obtained is 0.122 g.

$^1$H NMR CDCl$_3$ Fast Isomer: δ7.47-7.22(m,10H), 5.35(ABq,2H), 4.05(m,1H), 3.77(dd,1H), 3.60(ABq,2H), 3.39(m,1H), 2.53(m,1H), 2.33(m,1H), 1.55(m,1H), 0.94(s,9H), 0.83(s,9H), 0.21-0.02(4s,3H each). Slow Isomer: δ7.45-7.16 (m,10H), 5.4(d,1H), 5.27(d,1H), 4.18-3.96(m,2H), 3.8(m,1H), 3.57(d,1H), 3.43(d,1H), 2.79(m,1H), 2.5-1.99(m,2H), 1.08(d,3H), 0.95(s,9H), 0.87(s,9H), 0.25-0.04(4s,3H each).

EXAMPLE 14

Acetic acid, (dimethoxyphosphinyl)hydroxy-, phenylmethyl ester

The title compound was prepared by the procedure of E. Nakamura (Tet. Let. vol. 22, 1981, p. 663) benzyl glyoxalate (4.9 g) and dimethyl phosphite in 20 ml benzene are treated with catalytic p-toluenesulfonic acid. The mixture is refluxed with a Dean-Stark trap for 1 hour 30 minutes. After cooling, the reaction is concentrated and the residue chromatographed on silica gel with 10% hexanes in ethyl acetate to 100% ethyl acetate. The alcohol, 4.9 g, is obtained as a light yellow oil.

$^1$H NMR (CDCl$_3$) δ7.45-7.30(m,5H), 5.3(ABq,2H), 4.65(br d,1H), 3.9-3.7(4s,br s,7H).

EXAMPLE 15

Acetic acid, (dimethoxyphosphinyl)[[(1,1-dimethylethyl)dimethylsilyl]oxy]-. phenylmethyl ester Silylation of the alcohol described in Example 14 is effected by dissolving 3.66 g in dimethylformamide (13 ml) and adding tert-butyldimethylsilyl chloride (2.21 g) and imidazole (2.27 g). After stirring at room temperature for 1 hour and 30 minutes, the reaction is diluted with diethyl ether and washed five times with water once with brine and dried over anhydrous magnesium sulfate. Filtration and concentration gave 4.88 g of the title compound as a nearly colorless oil.

$^1$H NMR (CDCl$_3$) δ7.45-7.3(m,5H), 5.25(ABq,2H), 4.67(d,1H), 3.81(d,3H), 3.77(d,3H), 0.91(s,9H), 0.09(s,3H), 0.085(s,3H).

EXAMPLE 16

Acetic acid, (dimethoxyphosphinyl)hydroxy-, (4-nitrohpenyl)methyl ester

The title compound is prepared using the method described for Example 14. P-nitrobenzyl glyoxalate (4.32 g) and dimethylphosphite (2.0 ml) in 25 ml benzene are treated with catalytic p-toluenesulfonic acid. The mixture is refluxed with a Dean-Stark trap for 1 hour and 30 minutes. After cooling, the solvent is removed in vacuo. The resulting crystalline mass is slurried in ethyl acetate and filtered. The white crystals obtained amounted to 3.48 g.

$^1$H NMR (CDCl$_3$) δ8.30(d,2H), 7.73(d,2H), 5.42(ABq,2H), 4.91(d,1H), 3.75(2d,6H).

EXAMPLE 17

Acetic acid, (dimethoxyphosphinyl)[[(1,1-dimethylethyl)dimethylsilyl]oxy]-, (4-nitrophenyl)methyl ester The alcohol prepared in Example 16 (3.48 g) is dissolved in 12 ml dimethylformamide and treated with 1.81 g t-butyldimethylsilyl chloride and 1.86 g imidazole. After stirring at room temperature for 2 hours, the reaction is diluted with 50% ethyl acetate/diethyl ether and washed five times with water, once with saturated sodium bicarbonate, and once with brine. After drying over magnesium sulfate and filtration, the solvent is removed in vacuo to afford 3.90 g of silylated product as faintly yellow crystals.

$^1$H NMR (CDCl3) δ8.23(d,2H), 7.59(d,2H), 5.35(ABq,2H), 4.71(d,1H), 3.84(d,3H), 3.61(d,3H), 0.91(s,9H), 0.11(s,3H), 0.09(s,3H).

EXAMPLE 18

2-Butenoic acid,
4-[1-[(1,1-dimethylethyl)dimethylsilyl]-3-[1-[[(1,1-dimethylethyl)dimethylsilyl]oxy]-, phenyl methyl ester.
[2R-2α(E),3β(R*)]]-

Horner-Emmons reagent as prepared in Example 15 (0.111 g) in 60 ml dry tetrahydrofuran under argon is cooled to −40° C. and treated with lithium bis(trimethylsilyl)amide (0.311 ml of 1 M solution in tetrahydrofuran). After 5 minutes, the aldehyde 2-azetidineacetaldehyde, 3-[1-[[(1,1-dimethylethyl)dimethylsilyl]oxy]ethyl]-4-oxo-1-(triethylsilyl)-, [2R-[2α,3β(R*)]]- in 0.4 ml tetrahydrofuran is added dropwise and the cooling bath is allowed to gradually warm to 0° C. (30 minutes). The reaction is diluted with Et$_2$O and quenched with water. The organic phase is washed once with water, once with brine and dried over anhydrous magnesium sulfate. After filtration and concentration in vacuo the crude residue is purified by filtration through silica gel eluting with 10% ethyl acetate in hexanes.

Yield: 160 mg (95%) of nearly colorless oil, mixture of E:Z isomers=82:18 from NMR.

$^1$H NMR (CDCl$_3$) δ7.43–7.25(m,5H), 6.0(t,1H,minor Z isomer), 5.45(t,1H), 5.2(s,2H), 4.1(m,1H), 3.7(m,1H), 3.0–3.1(m,1H), 2.8(m,1H), 2.58(m,1H), 1.14(d,3H), 1.09(d,3H, minor Z isomer), 0.94(s,9H), 0.88(s,9H), 0.87(s,9H), 0.2(s,6H), 0.06(s,12H).

EXAMPLE 19

2-Pentenoic acid,
4-[1-[1,1-dimethylethyl)dimethylsilyl]-3-[1-[[1,1-dimethylsilyl]oxy]-2-azetidinyl]-2-[[(1,1-dimethylethyl)dimethylsilyl]-oxy]-, phenylmethyl ester,
[2R-[2α[S*-(E),3β(R*)]]-

The title compound is prepared by the procedure described in Example 18 by using an alternate aldehyde 2-azetidineacetaldehyde, 1-[(1,1-dimethylethyl)dimethylsilyl]-3-[1-[[(1,1-dimethylethyl)dimethylsilyl]oxy][2R$^2$α(R*),3β(R*)]]-.

$^1$H NMR (CDCl$_3$) δ7.36(m,5H), 5.45(d,1H), 5.18(s,2H), 4.06(t,1H), 3.64(m,1H), 3.5(br s,1H), 2.88(dd,1H), 1.26(d,3H), 1.05(d,3H), 0.91(s,9H), 0.88(s,18H), 0.19–0.0(m,18H).

EXAMPLE 20

2-Pentenoic acid.
4-[1-[(1,1-dimethylethyl)dimethylsilyl]-3-[1-[[(1,1-dimethylethyl)dimethylsilyl]oxy]ethyl]-4-oxo-2-azetidinyl]-2-[[(1,1-dimethylethyl) dimethylsilyl]oxy]-, (4-nitrophenyl)methyl ester,
[2S-[2α(S*-E),3β(S*)]]-E/Z ratio 88:12

The title compound is prepared by the procedure described in Example 18 by substituting the aldehyde with 2-azetidineacetaldehyde, 1-[(1,1-dimethylethyl)dimethylsilyl]-3-[1-[[(1,1-dimethylethyl)dimethylsilyl]oxy][2R$^2$α(R*),3β(R*)]]- and the Horner-Emmons reagent with that one prepared in Example 17.

$^1$H NMR (CDCl$_3$) E isomer: δ8.2(d,2H), 7.6(d,2H), 5.5(d,1H), 5.27(s,2H), 4.07(m,1H), 3.64(m,1H), 3.52(m,1H), 2.88(m,1H), 1.27(d,3H), 1.06(d,3H), 0.92(s,9H), 0.91(s,9H), 0.89(s,9H), 0.21(s,3H), 0.1(s,3H), 0.09(s,3H), 0.087(s,3H), 0.07(s,3H), 0.06(s,3H), Z isomer: δ8.2(d,2H), 7.49(d,2H), 6.07(d,1H), 5.28(q,2H), 4.09(m,1H), 3.56(m,1H), 3.18(m,1H), 2.93(dd,1H), 2.5(d,3H), 1.08(d,3H), 0.95(s,9H), 0.92(s,9H), 0.89(s,9H), 0.17(s,3H), 0.165(s,3H), 0.16(s,3H), 0.14(s,3H), 0.09(s,3H), 0.06(s,3H).

EXAMPLE 21

2-Azetidinebutanoic acid,
β-bromo-1-(1,1-dimethylethyl)dimethylsilyl]3-[1-[(1,1-dimethylethyl)dimethylsilyl]oxy]ethyl]-γ-methyl-α,4-dioxo-, (4-nitrophenyl)methyl ester, [2S-2α[S*(R*) and S*(S*),3β(S*)]]-

The silyl enol ether from Example 20 (38.1 mg) is dissolved in 0.5 ml dry tetrahydrofuran under argon and cooled in an ice bath. To this solution is added bromine (0.004 ml) dropwise. After stirring for 15 minutes, the reaction is quenched with 10% sodium thiosulfate and diluted with ethyl acetate. After washing once with brine the organic layer is dried over anhydrous magnesium sulfate and filtered. The residue obtained upon concentration is purified via flash chromatography on silica gel (20% ethyl acetate in hexanes). The pure bromide as a mixture of diastereomers (4:1) is obtained in quantitative yield.

$^1$H NMR (CDCl$_3$) δ8.26(d,2H), 7.59(d,2H), 5.48–5.36-(ABq and d,3H), 5.05(d, minor isomer), 4.12–4.02(m,1H), 3.67(t,1H), 3.43(m,1H), 2.87(m, minor isomer), 2.58(m,1H), 1.25(d,3H), 1,18(d,3H), 1.08(d, minor isomer), 0.98(s, minor isomer), 0.91(s,9H), 0.89(s,9H), 0.88(s, minor isomer), 0.33,0.26,0.07(3s, minor isomer), 0.21(s,3H), 0.13(s,3H), 0.1(s,3H), 0.06(s,3H).

EXAMPLE 22

2-Azetidinebutanoic acid,
β-bromo-1-[(1,1-dimethylethyl)dimethylsilyl]3-[1-[(1,1-dimethylethyl)dimethylsilyl)oxy]ethyl]-α,4-dioxo-, phenylmethyl ester, [2R-[2α,3β(R*)]]-

The title compound is prepared by the procedure described in Example 21 by substituting the silyl enol ether from Example 18 for that one used in Example 21.

$^1$H NMR (CDCl$_3$) δ7.40(m,5H), 5.35(ABq,2H), 4.95(dd,1H), 4.15(m,1H), 3.85(m,1H), 2.76(m,1H), 2.46(m,1H), 2.17(m,1H), 1.26(d,3H), 0.96(s,9H), 0.92(s,9H), 0.26(s,3H), 0.22(s,3H), 0.11(s,3H), 0.10(s,3H).

EXAMPLE 23

2-Azetidinebutanoic acid,
β-bromo-1-[(1,1-dimethylethyl)dimethylsilyl]3-1-(1,1-dimethylethyl)dimethylsilyl]oxy]ethyl]-γ-methyl-α,4-dioxo-, phenylmethyl ester, [2S-[2α[S*(R*) and S*(S*)], 3β(S*)]]-

The title compound is prepared by the procedure described in Example 21 by substituting the silyl enol ether from Example 19 for the one used in Example 21.

$^1$H NMR (CDCl$_3$) δ7.4(m,5H), 5.45–5.26(m,3H), 5.02(d, minor isomer), 4.08(m,1H and 2H minor isomer), 3.67(t,1H), 3.44(m,1H), 2.86(m, minor isomer), 2.68–2.5(m,1H+1H minor isomer), 0.97(s, minor isomer), 0.9(s,9H), 0.89(s,9H), 0.88(s, minor isomer), 0.31,0.24,0.09,0.07(s, minor isomer), 0.2(s,3H), 0.12(s,3H), 0.09(s,3H), 0.06(s,3H).

EXAMPLE 24

2-Azetidinebutanoic acid,
1-(1,1-dimethylethyl)dimethylsilyl]3-[1-[[(1,1-dimethylethyl)dimethylsilyl]oxy]ethyl]-γ-methyl-α,4-dioxo-β-[(phenylmethyl)thio]-, phenylmethyl ester,
[2S-[2αS*(R* or S*),3β(S*)]]-

Bromide prepared as in Example 23 (0.483 g) is dissolved in 6.5 ml of dry tetrahydrofuran under argon and treated with benzyl mercaptan (0.1 ml). Triethylamine (0.12 ml) is added to the mixture and the reaction is stirred at room temperature for 20 minutes. After dilution with ethyl acetate and quenching with saturated sodium bicarbonate, the organic layer is washed once with water and once with brine. The residue obtained after drying over magnesium sulfate, filtration and concentration is chromatographed on silica gel with 10% ethyl acetate in hexanes. The two diastereomers are separated yielding 0.078 g of minor isomer and 0.365 g of major isomer. Overall yield 0.443 g (86%).

IR(Neat) 1744 cm$^{-1}$
$^1$H NMR (CDCl$_3$) δ7.44–7.17(m,10H+minor isomer), 5.32(s,2H), 5.28(s, minor isomer), 4.23(d, minor isomer), 4.14(m,1H), 4.09(m,1H), 3.83(d,1H), 3.59(d,1H), 3.36(d,1H), 2.66(m,1H), 2.45(m,1H), 1,15(d,3H), 1.03(d,3H), 0.93(s,9H), 0.89(s,9H), 0.21(s,3H), 0.16(s,3H), 0.08(s,3H), 0.05(s,3H).

EXAMPLE 25

2-Azetidinebutanoic acid,
1-[(1,1-dimethylethyl)dimethylsilyl]-3-[1-[[(1,1-dimethylethyl)dimethylsilyl]oxy]ethyl]-γ-methyl-α,4-dioxo-β-(phenylthio)-, phenylmethyl ester,
[2S-[2α(S*),3β(S*)]]-

A solution of the compound prepared in Example 23 (220 mg) and thiophenol (0.04 ml) in 3 ml dry tetrahydrofuran under argon is treated with diisopropylethylamine (0.092 ml). After 30 minutes the reaction is quenched with saturated sodium bicarbonate solution and diluted with ethyl acetate. The organic layer is subsequently washed once with water and once with brine. After drying over anhydrous magnesium sulfate, filtration and concentration, the residue is chromatographed on silica gel with 10% EtoAc in hexanes. The mixture of diastereomers obtained amounted to 190 mg (83%).

IR(Neat) 1744 cm$^{-1}$
$^1$H NMR (CDCl$_3$) δ7.45–7.24(m,10H), 5.3(ABq,2H), 4.39(m,1H), 4.30(d,1H), 4.17(m,1H), 2.84(m,1H), 2.36(m,1H), 1,16(d,3H), 1.02(d,3H), 0.94(s,9H), 0.93(s,9H), 0.24(s,3H), 0.19(s,3H), 0.11(s,3H), 0.09(s,3H).

EXAMPLE 26

2-Azetidinebutanoic acid,
β-(cyclopentylthio)-1-[(1,1-dimethylethyl)dimethylsilyl]-3-[1-[[(1,1-dimethylethyl)dimethylsilyl]oxy]ethyl]-α,4-dioxo-, phenylmethyl ester, [2R-[2α(R* and γ*),3β(R*)]]-

To a solution of the bromide prepared in Example 22 (0.135 g) in 2 ml dry tetrahydrofuran at 0° C. under argon is added cyclopentylmercaptan (0.026 ml). To this mixture is added dropwise sodium bis(trimethylsilyl)amide (0.265 ml of 1 M solution in tetrahydrofuran). After 15 minutes, the reaction is quenched with 10% acetic acid and diluted with diethyl ether. The organic layer is washed once with water, once with brine, and dried over anhydrous magnesium sulfate. After filtration and concentration, the resulting residue is chromatographed on silica gel with 10% ethyl acetate in hexanes. The title compound is obtained as a mixture of diastereomers 0.109 g (78%).

IR 1746 cm$^{-1}$
$^1$H NMR (CDCl$_3$) δ7.41(m,10H), 5.33(2ABq,4H), 4.14(m,2H), 3.99(m,1H), 3.91(m,1H), 3.85(m,1H), 3.50(m,1H), 2.88(m,1H), 2.81(m,1H), 2.77(m,1H), 2.67(m,1H), 2.26(m,1H), 2.12(m,1H), 2.0–1.3(m,18H), 1.12(d,3H), 1.08(d,3H), 0.96(s,9H), 0.95(s,9H), 0.88(s,9H), 0.84(s,9H).

EXAMPLE 27

2-Azetidinebutanoic acid,
1-(1,1-dimethylethyl)dimethylsilyl]-3-[1-[(1,1-dimethylethyl)dimethylsilyl]oxy]ethyl]-α,4-dioxo-β-(2-pyrimidinylthio)-, phenylmethyl ester, [2R-[2α(R* and S*), 3β(R*)]]-

The title compound is prepared using a procedure analogous to that one described in Example 26 wherein 2-mercaptopyrimide is used instead of cyclopentyl mercaptan.

IR 1743 cm$^{-1}$
$^1$H NMR (CDCl$_3$) mixture of diastereomers δ8.38-(minor,d,2H), 8.18(d,2H), 7.44–7.27(major/minor,m,10H), 6.99(minor,t,1H), 6.89(t,1H), 5.4(d,1H), 5.28(d,1H), 5.25(minor,ABq,2H), 5.18(minor,dd,1H), 4.85(dd,1H), 4.21(minor,m,1H), 4.1(m,1H), 3.8(m,1H), 3.63-(minor,m,1H), 3.02(minor,dd,1H), 2.94(dd,1H), 2.80(minor,m,1H), 2.3–2.04(m,2H), 1.89(minor,m,1H), 0.95(minor,s,9H), 0.93(s,9H), 0.85(minor,s,9H), 0.79(s,9H).

EXAMPLE 28

2-Azetidinebutanoic acid.
1-[(1,1-dimethylethyl)dimethylsilyl]-3-[1-[[(1,1-dimethylethyl)dimethylsilyl]oxy]ethyl-β-[(3-ethoxy-3-oxopropyl)thio-γ-methyl-α,4-dioxo-phenylmethyl ester, [2S-[2α(S*), 3β(S*)]]-

The title compound is prepared using a procedure analogous to Example 24 wherein ethyl 3-mercaptopropionate is substituted for benzyl mercaptan. IR (neat) 1741 cm$^{-1}$
$^1$H NMR (CDCl$_3$) mixture of diastereomers δ7.4(m,5H), 5.4–5.25(m,2H), 4.22–3.98(m,5H), 3.3–2.3(m,6H), 1.25(m,6H), 0.95(s,9H), 0.89(s,9H).

EXAMPLE 29

1,2-pyrazolidinedicarboxylic acid,
4-[[1-[1-[(1,1-dimethylethyl)dimethylsilyl]-3-[1-[[(1,1-dimethylethyl)dimethylsilyl]oxy]ethyl]-4-oxo-2-azetidinyl]-ethyl]-3-[(4-nitrophenyl)methoxy]-2,3-dioxopropyl]thio]-, bis(4-nitrophenyl)methyl]ester,
[2S-2α[S*(R*) and S*(S*),3β(S*)]-

The title compound is prepared via the procedure described in Example 26 by using the bromide from Example 21 and 1,2-pyrazolidinedicarboxylic acid, 4-mercapto-, bis[(4-nitrophenyl)methyl]ester.

IR (neat) 1738 cm$^{-1}$
$^1$H NMR (CDCl$_3$) mixture of diastereomers δ8.35–8.1(m,6H), 7.65–7.40(m,6H), 5.45–5.15(m,6H), 4.4–2.55(m,10H), 1.35–0.85(m,24H).

EXAMPLE 30

2-Azetidinebutanoic acid,
β-(2-benzoxazolylthio)1-[(1,1I-dimethylethyl)dimethylsilyl]-3-[1-[[(1,1-dimethylethyl)dimethylsilyl]oxy]ethyl]-γ-methyl-α,4dioxo-,(4-nitrophenyl)methyl ester, [3S-[2(S*), 3β(S*)]]-

The title compound is prepared using the method described in Example 26 by substituting the bromide prepared in Example 21 for the one used in Example 26 and using 2-mercaptobenzoxazole instead of cyclopentyl mercaptan.

$^1$H NMR (CDCl$_3$) major isomer: δ8.05(d,2H), 7.42(d,2H), 7.42(d,2H), 7.35(m,2H), 7.20(m,2H), 5.55(d,1H), 5.26(s,1H), 4.0(m,1H), 3.66(m,1H), 3.35(m,1H), 2.82(m,1H), 1.20(m,6H), 0.95(s,9H), 0.85(s,9H), 0.25-0(4s,3H each).

EXAMPLE 31

2-Azetidinebutanoic acid,
1-[(1,1-dimethylethyl)dimethylsilyl]-3-[1-[[(1,1-dimethylethyl)dimethylsilyl]oxy]ethyl]-β-(2-hydroxyethyl)thio]-γ-methylα,4-dioxo-,(4-nitrophenyl)methyl ester, [2S-[2α[β-R* (or S*),γ-S[*3β(S*)]]-

The title compound is prepared via the method described in Example 24 by substituting the bromide prepared in Example 21 for the one used in Example 24 and using 2-mercaptoethanol instead of cyclopentyl mercaptan.

$^1$H NMR mixture of diastereomers: δ8.26(d,2H), 7.58(d,2H), 5.37(q,2H), 4.3-3.4(m,6H), 3.15-2.4(m,3H), 1.25(d,3H), 1,17(d,3H), 0.93(s,9H), 0.89(s,9H), 0.18(s,6H), 0.08(d,6H).

EXAMPLE 32

1-Azabicyclo[3.2.0]hept-2-ene-2-carboxylic acid, 6-[1-[[(1,1-dimethylethyl)dimethylsilyl]oxy]ethyl]4-methyl-7-oxo-2-[(phenylmethyl)thio]-,phenylmethyl ester,[4R-[4α,5β, 6β(R*)]]-

The α-keto ester from Example 24 (0.129 g) is dissolved in 3 ml of acetonitrile and treated with triethylamine trishydrofluoride (0.21 ml). After one hour, the reaction is quenched by pouring the mixture into rapidly stirring saturated sodium bicarbonateethyl acetate. The organic layer is separated and washed once with water and once with brine. After drying over magnesium sulfate and filtration the solvents are removed in vacuo to give 0.102 g of crude N-H β-lactam. This material is used in the cyclization step without further purification.

The crude N-H β-lactam (.102 g) is dissolved in 1.3 ml of dry tetrahydrofuran under argon and treated with titanium tetrachloride (0.735 ml of a 1 M solution in methylene chloride). After stirring at room temperature for 1 hour and 45 minutes, the reaction mixture is poured into rapidly stirring saturated sodium bicarbonate-ethyl acetate. The organic layer is then washed once with water and twice with brine. The crude residue obtained after drying over anhydrous magnesium sulfate, filtration, and concentration is chromatographed on silica gel with 20% ethyl acetate in hexanes. The pure carbapenem is obtained as white crystals 0.056 g (55%).

M.P. 116°-8° C.
$^1$H NMR (CDCl$_3$) δ7.47-7.28(m,10H), 5.28(ABq,2H), 4.20(m,1H), 4.18-4.04(m,3H), 3.30(m,1H), 3.19(m,1H), 1.23(2d,6H), 0.85(s,9H), 0.06(s,3H), 0.04(s,3H). MS(FAB) 537 (M+)

EXAMPLE 33

1-azabicyclo[3.2.0]hept-2-ene-2-carboxylic acid,6-(1-hydroxyethyl)-4-methyl-7-oxo-3-(phenylthio)-, phenylmethyl ester. [4R-[4α,5β,6β(R*)]]-

The α-keto ester prepared in Example 25 (0.0837 g) in 0.6 ml acetonitrile is added to 4 ml of 10% hydrofluoric acid in acetonitrile. After 30 minutes the reaction is poured into rapidly stirring ethyl acetate-saturated sodium bicarbonate solution. Additional saturated sodium bicarbonate solution is added until the originally cloudy solution is clarified. The organic layer is washed once with water, once with brine and dried over anhydrous magnesium sulfate. Filtration and concentration afforded 0.053 g of crude deprotected product as a light yellow oil. The crude product is dissolved in 0.9 ml of dry tetrahydrofuran under argon and treated with titanium tetrachloride (0.624 ml of a 1.0 M solution in dichloromethane). After 3 hours the reaction mixture is poured into rapidly stirring ethyl acetate-saturated sodium bicarbonate. The mixture is partitioned and the organic layer washed twice with brine and dried over anhydrous magnesium sulfate. Filtration and concentration affords the crude carbapenem which is purified via silica gel chromatography (40% ethyl acetate in hexanes). The title compound is obtained as white crystals (0.0143 g).

$^1$H NMR (CDCl$_3$) δ7.6-7.25(m,10H), 5.34(ABq,2H), 4.25-4.1(m,2H), 3.18(dd,1H), 3.06(m,1H), 1.29(d,3H), 0.96(d,3H).

EXAMPLE 34

1-Azabicyclo[3.2.0]hept-2-ene-2-carboxylic acid,3-(cyclopentylthio)-6-(1-hydroxyethyl)-7-oxo-, phenylmethyl ester, [5R-[5α,6α(R*)]]-

The title compound is prepared from the α-keto ester of Example 26 using the procedure described in Example 33.

$^1$H NMR (CDCl$_3$) δ7.51-7.15(m,5H), 4.2(m,2H), 3.5-3.0(m,4H), 2.2-1.4(m,8H), 1.35(d,3H).

EXAMPLE 35

1-Azabicyclo[3.2.0]hept-2-ene-2-carboxylic acid,3-(2-benzoxazolylthio)-6-(1-hydroxyethyl)-4-methyl-7- oxo-, (4-nitrophenyl)methyl ester, [4R-[4α,5β,662 (R*)]]-

The title compound is prepared from the α-keto ester of Example 26 using the procedure used in Example 33.
IR (neat) 1773 cm$^{-1}$
$^1$H NMR (CDCl$_3$) δ8.25(d,2H), 7.65(d,2H), 7.40(m,2H), 7.15(m,2H), 5.55-5.30(ABq,2H), 4.46(m,1H), 4.30(m,1H), 4.00(m,1H), 3.40(m,1H), 1.35(d,3H), 1,15(d;3H).

EXAMPLE 36

1,2-Pyrazolidinedicarboxylic acid, 4-[[6-(1-hydroxyethyl)-4-methyl-2-[(4-nitrophenyl)methoxy]carbonyl]-7-oxo-1-azabicyclo[3.2.0]hept-2-en-3-yl]thio]-,bis[(4-nitrophenyl]methyl]ester, [4R-[4α,5β,6β(R)]]-

The title compound is prepared from the α-keto ester of Example 29 using the procedure described in Example 33.
IR (neat) 3500, 1770 cm$^{-1}$ ¹H NMR (CDCl₃) δ8.33–8.10(m,6H), 7.7–7.4(m,6H), 5.55–5.15(m,6H), 4.4–3.98(m,5H), 3.75–3.15(m,5H), 1.37(d,3H), 1.25(m,3H).

EXAMPLE 37

1-Azabicyclo3.2.0]hept-2-ene-2-carboxylic acid, 6-(1-hydroxyethyl)-3-[(2-hydroxyethyl)thio]4-methyl-7-oxo-,(4-nitrophenyl)methyl ester, [4R-[4α,5β,6β(R*)]]-

The title compound is prepared from the α-keto ester of Example 31 using the procedure described in Example 33.

¹H NMR (CDCl₃) δ8.22(d,2H), 7.65(d,2H), 5.38(q,2H), 4.25(m,1H), 3.84(m,1H), 3.29(m,1H), 3.05(m,5H), 1.38(d,3H), 1.24(d,3H).

EXAMPLE 38

2-Azetidinebutanoic acid, 1-[(1,1-dimethylethyl)dimethylsilyl]-3-[1-[[(1,1-dimethylethyl)dimethylsilyl]oxy]ethyl]-α,4-dioxo-β-[(phenylmethyl)thio]-, phenylmethyl ester, 2R-[2α(R* and S*), 3β(R*)]]-

A mixture of the epoxide from Example 39 (50 mg) benzyl mercaptan (0.05 ml), and diethyl isopropylamine (0.05 ml) in tetrahydrofuran (1.0 ml) is stirred at room temperature (argon atmosphere) for 22 hours. The products are isolated by preparative thin layer chromatography on silica gel using ethyl acetate:hexanes (1:4). Thin layer chromatography and 300 MHz NMR spectroscopy showed that the two diastereomers are the same as those obtained in Example 13.

EXAMPLE 39

Oxiranecarboxylic acid, 2-chloro-3-[1-[1-[((1,1-dimethylethyl)dimethylsilyl]-3-[1-[[(1,1-dimethylethyl)dimethylsilyl]oxy]ethyl]4-oxo-2-azetidinyl]ethyl]-,(4-nitrophenyl)methyl ester,[3S-[2(S*), 3β(S*)]]-

Hexamethylphosphorous triamide (0.63 ml) is added to a stirred mixture of the aldehyde used in Example 5 (1.39 g) and p-nitrobenzyl trichloroacetate (1.04 g) in 10 ml of tetrahydrofuran at −78° C. (argon atmosphere). The reaction mixture is stirred at this temperature for 1.25 hours, then quenched with a solution of 0.20 ml of acetic acid in 1.0 ml of tetrahydrofuran. The reaction is worked-up as described in Example 41 and purified by chromatography on silica gel using ethyl acetate:hexanes (1:4) to give the desired epoxide.

¹H NMR (CDCl₃) δ8.24(d,2H), 7.55(d,2H), 5.35(s,2H), 4.12(m,1H), 3.68(m,1H), 3.42(d,1H), 2.40(m,1H), 1.35(d,3H), 1,15(d,3H), 0.95(s,9H), 0.85(s,9H), 0.20–0(4s,3H each).

EXAMPLE 40

2-Butenoic acid, 2-chloro-4-[1-[(1,1-dimethylethyl)dimethylsilyl]-3-[1-[[(1,1-dimethylethyl)dimethylsilyl]oxy]ethyl]4-oxo-2-azetidinyl]-benzyl ester, [3S(S*)]-

The desired alkene is prepared by the same method outlined in Example 45 except that the reaction mixture is allowed to stir at room temperature overnight.

¹H NMR (CDCl₃): δ7.40(s,5H), 7.07(t,1H), 5.30(d,2H), 4.05(m,1H), 3.70(m,1H), 2.95–2.80(broad m,2H), 2.55(m,1H), 1,17(d,3H), 0.97(s,9H), 0.88(s,9H), 0.28–0(4s,3H each).

EXAMPLE 41

2-Azetidinebutanoic acid, α, α-dichloro-1-(1,1-dimethylethyl)dimethylsilyl]-3-[1-[[(1,1-dimethylethyl)dimethylsilyl]oxy]ethyl]-β-hydroxy-4-oxo-,phenylmethyl ester, [3S-[3α(S*)]]-

A solution of lithium hexamethyl disilazide (1.2 ml of a 1.0 M solution) is added dropwise to a solution of benzyl dichloroacetate (219 mg) and the aldehyde used in Example 5 in tetrahydrofuran (5 ml) in an ice bath. The mixture is stirred for 1.0 hour in the cold then quenched with 0.12 ml of acetic acid. The reaction mixture is poured into 0.5 M potassium dihydrogen phosphate and extracted with ethyl acetate. The organic phase is washed with brine, dried (magnesium sulfate) and evaporated to dryness. Trituration of the residue with hexane afforded the dichloro hydroxy compound which is collected by filtration.

¹H NMR (CDCl₃) δ7.38(s,5H), 5.31(d,2H), 4.26(m,1H), 4.06(m,1H), 3.73(m,1H), 2.88(d,1H), 2.71(t,1H), 2.18(m,1H), 1.79(m,1H), 1.22(d,3H), 0.95(s,9H), 0.88(s,9H), 0.23–0(4s,3H each).

EXAMPLE 42

Oxiranecarboxylic acid, 2-chloro-3-[1-[(1,1-dimethylethyl)dimethylsilyl]-3-[1-[[(1,1-dimethylethyl)dimethylsilyl]oxy]ethyl]4-oxo-2-azetidinyl]methyl]-,phenylmethyl ester, 3S-[3α(S*)]]-

The filtrate from the above experiment in Example 41 evaporated to dryness and chromatographed on silica gel using ethyl acetate:hexanes (1:4) to give the epoxide product.

¹H NMR (CDCl₃) 7.32(s,5H), 5.19(d,2H), 4.07(m,1H), 3.72(m,1H), 3.40(m,1H), 2.88(m,1H), 2.17(m,1H), 2.01(m,1H), 1.08(d,3H), 0.90(s,9H), 0.80(s,9H), 0.2–0(4s,3H each).

EXAMPLE 43

Oxiranecarboxylic acid, 2-chloro-3-[[1-[(1,1-dimethylethyl)dimethylsilyl]-3-[1-[[(1,1-dimethylethyl)dimethylsilyl]oxy]ethyl]4-oxo-2-azetidinyl]methyl]-, phenylmethyl ester, 3S-[3α(S*)]]-

A solution of potassium hexamethyldisilazide (0.60 ml of 1.0 M solution in tetrahydrofuran) is added to a solution of the hydroxy-dichloro compound (302 mg) (prepared as described in Example 41) in 2.5 ml of tetrahydrofuran (argon atmosphere) at 0° C. The reaction mixture is allowed to come to −20° C. and worked-up as described in Example 41. The product is identical to that obtained in Example 39 as shown by 300 MHz NMR spectroscopy.

EXAMPLE 44

Oxiranecarboxylic acid, 2-chloro-3-[[1-[(1,1-dimethylethyl)dimethylsilyl]-3-[1-[(1,1-dimethylethyl)dimethylsilyl]oxy]ethyl]4-oxo-2-azetidinyl]methyl]-,phenylmethyl ester, 3S-[3α(S*)]]-

The alkene described in Example 40 is converted to the epoxide by the method described by M. Ashwell et al., Tetrahedron 21, 7429 (1990). This compound is identical to the material prepared in Example 39 as shown by 300 MHz NMR spectroscopy.

EXAMPLE 45

2-Azetidinebutanoic acid,
α,α-dichloro-1-[(1,1-dimethylethyl)dimethylsilyl]-3-[1-[[(1,1-dimethylethyl)dimethylsilyl]oxy]ethyl]-γ-methyl-β-hydroxy-4-oxo-, phenylmethyl ester,
[3S-[2(S*).3α(S*)]]-

A solution of the aldehyde used in Example 19 (545 mg) and benzyl trichloroacetate (414 mg) in 5 ml of tetrahydrofuran is added to a stirred mixture (argon atmosphere) of zinc (266 mg) and diethyl aluminum chloride (0.38 ml of 1.8 M solution) in 10 ml of tetrahydrofuran at 0° C. The mixture is stirred for an additional 30 minutes in the cold then ethyl acetate and pyridine (0.30 ml) are added. The resulting mixture is washed with 1.0 N hydrochloric acid, water, and brine then dried over magnesium sulfate. Evaporation of the solvent followed by chromatography on silica gel using 15% ethyl acetate:hexanes afforded 412 mg of the hydroxy dichloro compound.

$^1$H NMR (CDCl$_3$): δ7.38(s,5H), 5.31(d,2H), 4.59–4.56(dd,1H), 3.96(m,1H), 3.47(m,1H), 3.34(dd,1H), 2.93(d,0H), 2.57(m,1H), 1.27(d,3H), 1,14(d,3H), 0.97(s,9H), 0.87(s,9H), 0.26–0(4s,3H each). D$_2$O exchange resulted in the disappearance of the δ 2.93 doublet and the peat at 4.59–4.56 became a broad singlet.

EXAMPLE 46

2-Azetidinebutanoic acid,
β-cyano-1-[(1,1-dimethylethyl)dimethylsilyl]-3-[1-[[(1,1-dimethylethyl)dimethylsilyl]oxy]ethyl]-α,4-dioxo-, phenylmethyl ester, [2R-[2α(R* or S*),3β(R*)]]-

A solution of the bromide from Example 22 (190 mg) and 18 mg sodium cyanide in 1 ml of dimethylformamide is stirred at room temperature under argon for one hour. The solution is diluted with 20 ml of ethyl acetate and is washed with 1 N hydrochloric acid, water and brine. The organic layer is dried over magnesium sulfate, filtered and concentrated in vacuo to an oil. Purification is carried out on 2000 micron silica plates developing with hexane:ethyl acetate:70:30 to afford 60 mg of the desired product.

C.I.M.S.: M+559

NMR (CDCl$_3$) δ0.8(s,9H), 0.9(s,9H), 1,1(d,3H), 2.4(m,1H), 2.9(m,1H), 3.5(m,1H), 3.8(m,1H), 5.25(s,2H), 7.35(s,5H).

EXAMPLE 47

2-Azetidinebutanoic acid,
β-cyano-3-(1-hydroxyethyl)α,4-dioxo-, phenylmethyl ester. [2R-[2α(R* or S*), 3β(R*)]]-

A solution of 90 mg of the bromide from Example 46 in 5 ml of 10% HF in acetonitrile is stirred at room temperature for 30 minutes. The solution is diluted with 30 ml of ethyl acetate and is washed with saturated bicarbonate solution and brine. The organic layer is dried over magnesium sulfate, filtered and is concentrated in vacuo to yield 47 mg of the desired product.

NMR (CDCl$_3$) δ1.22(d,2H), 2.05(m,1H), 2.55(m,1H), 2.90(m,1H), 3.60(m,1H), 3.90(m,1H), 5.25(s,2H), 6.90(s,1H), 7.40(s,5H).

EXAMPLE 48

2-Azetidinebutanoic acid,
1-[(1,1-dimethylethyl)dimethylsilyl]-3-1-[[(1,1-dimethylethyl)dimethylsilyl]oxy]ethyl]-β-methoxy-α,4-dioxo-, methyl ester, [2R-[2α,3β(R*)]]-, stereo isomers A solution of 215 mg of the bromide from Example 22 and 40 mg of diisopropylethylamine in 3 ml of methanol is stirred at room temperature for four hours under argon. The solution is diluted with ethyl acetate and is successively washed with 1 N hydrochloric acid, saturated sodium bicarbonate, and brine. The organic layer is dried over magnesium sulfate, filtered and is concentrated in vacuo to an oil. Purification is carried out on a silica column. Eluting with hexane:ethyl acetate:70:30 to yield 99 mg of the desired product as a white solid. NMR indicates a 4:1 ratio of diastereomers. The major isomer shows methoxyl absorption at 3.50 δ and 3.75 δ (CDCl$_3$).

We claim:

1. A process for producing a compound of the formula:

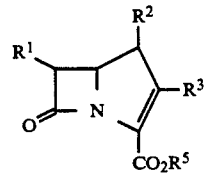

wherein:
R$^1$ is hydrogen, hydroxy (lower) alkyl or protected hydroxy (lower) alkyl;
R$^2$ is selected from the group consisting of hydrogen and (C$_1$–C$_6$) alkyl;
R$^3$ is hydrogen, halogen, azido, nitro, cyano, a suitable leaving group comprising a moiety selected from OCOCH$_3$, OCOCF$_3$, OSO$_2$CH$_3$, OSO$_2$Ph, OP(O)(OPh)$_2$;
a moiety of the formula —S(O)$_i$R$^a$, wherein i=0, 1, 2 and R$^a$ may be hydrogen, (C$_1$–C$_6$) alkyl, (C$_3$–C$_7$) cycloalkyl, (C$_2$–C$_6$) alkenyl, (C$_2$–C$_6$) alkenyl, aryl heteroaryl, aryl (C$_1$–C$_6$) alkanoyl, arylcarbonyl, heteroarylcabonyl, heterocyclyl, heterocyclyl (C$_1$–C$_6$) alkyl, fused heterocyclyl, fused heterocyclyl (C$_1$–C$_6$) alkyl, fused heteroaryl, fused heteroaryl (C$_1$–C$_6$) alkyl, quaternized heteroaryl, quaternized heteroaryl (C$_1$–C$_6$) alkyl, quaternized heterocyclyl, quaternized heterocyclyl (C$_1$–C$_6$) alkyl, quaternized fused heterocyclyl, quaternized fused heterocyclyl (C$_1$–C$_6$) alkyl, quaternized fused heteroaryl, quaternized fused heteroaryl (C$_1$–C$_6$) alkyl, quaternized heterocyclyl (C$_1$–C$_6$) thioalkyl, any of such groups being optionally substituted by C$_1$–C$_6$ alkyl, amino, C$_1$–C$_6$ alkanoylamino, mono-, di- and tri-(C$_1$–C$_6$) alkylamino, hydroxy, C$_1$–C$_6$ alkoxy, mercapto, C$_1$–C$_6$ alkylthio, heteroarylthio, fused heteroarylthio, arylthio, heterocyclylthio, fused heterocyclylthio, sulphamoyl, carbamoyl, amidino, quanidino, nitro, fluoro, chloro, bromo, carboxy and salts and esters thereof, C$_1$–C$_6$ alkanoyloxy, arylcarbonyl, heteroarylcarbonyl, heterocyclylcarbonyl, fused heterocyclylcarbonyl, the heteroatom or heteroatoms in the above-named heterocyclyl, fused heterocyclyl, heteroaryl and fused heteroaryl moieties are selected from 1–4 oxygen, nitrogen or sulfur atoms and each ring of the heterocycle, fused heterocycle and heteroaryl, fused heteroaryl moieties is comprised of 5 of 6 atoms, the heteroatom or heteroatoms in the above named quaternized heteroaryl, quaternized heteroaryl ($C_1$-$C_6$) alkyl, quaternized heterocyclyl, quaternized heterocyclyl ($C_1$-$C_6$) alkyl, quaternized fused heterocyclyl, quaternized fused heterocyclyl ($C_1$-$C_6$) alkyl, quaternized fused heteroaryl, quaternized fused heteroaryl ($C_1$-$C_6$) alkyl, quaternized heterocyclyl ($C_1$-$C_6$) thioalkyl moieties are selected from 1–4 oxygen, nitrogen or sulfur atoms and must contain at least one nitrogen atom and each ring of the respective moiety is comprised of 5 or 6 atoms; a moiety of the formula —$OR^a$, where $R^a$ is described hereinabove;

moieties of the formulae —$NR^hR^i$, —$N(R^h)OR^i$, —$N(R^h)NR^hR^i$,

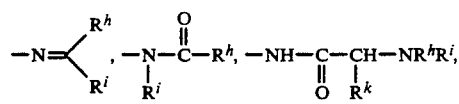

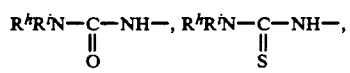

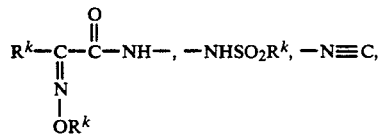

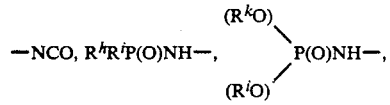

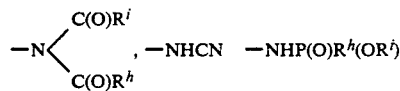

where $R^h$ and $R^i$ are independently selected from hydrogen; substituted or unsubstituted $C_1$-$C_4$ alkyl and cycloalkyl having from 1 to 6 carbon atoms, aryl, heterocyclyl, heterocyclyl ($C_1$-$C_4$) alkyl, heteroaryl and heteroaryl ($C_1$-$C_4$) alkyl wherein the heteroatom or heteroatoms are selected from 1–4 oxygen, nitrogen and sulfur atoms or $R^h$ and $R^i$ taken together may form a cyclic group consisting of 5 and 6 ring atoms and wherein $R^h$ and $R^i$ or the cyclic radical formed by their joinder may be substituted wherein the substituents are selected from the group consisting of amino, mono-, di- and tri-($C_1$-$C_3$) alkylamino, hydroxyl, carboxyl, alkoxyl, —$SO_2NH_2$, phenyl, benzyl, and alkoxylcarbonyl; wherein $R^k$ represents hydrogen, substituted or unsubstituted ($C_1$-$C_3$) alkyl, ($C_2$-$C_6$) alkenyl, heterocyclyl and heteroaryl wherein the heteroatom or heteroatoms are selected from 1–4 oxygen, nitrogen or sulfur and the cyclic portion has 5 or 6 ring atoms wherein the substituents on $R^k$ are selected from amino, mono-, di- and tri-($C_1$-$C_3$) alkylamino, hydroxyl, carboxyl, fluoro, $SO_2NH_2$ carboxamido and alkoxycarbonyl; moieties of the formulae:

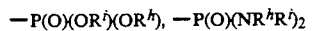

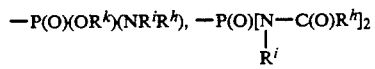

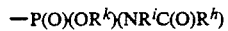

where $R^h$, $R^i$ and $R^k$ are as hereinbefore defined; moieties of the formulae:

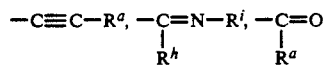

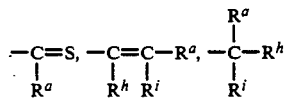

—$CH_2NR^iR^h$, —$CH_2N(R)OR^i$, $CH_2N(R^k)NR^hR^i$, —$CH_2$—F, —$CH_2Cl$, —$CHF_2$, —$CH_2Br$, —$CH_2I$, —$CH_2OCOCH_3$, —$CH_2N(R^i)C(O)R^i$, —$CH_2$—$N(R)^i$, $CH_2NHP(O)NR^hR^i$, —$CH_2$—$C(NOR^k)C(O)NR^hR^i$, —$CH_2NHSO_2R^k$, $CH_2NHP(O)(OR^i)(OR^h)$, —$CH_2$-$P(O)(OR^i)(OR^h)$, —$CH_2P(O)(NR^hR^i)$, —$CHR^kNR^iR^h$, —$CHR^kN(R^h)OR^i$, —$CHR^kN(R^k)NR^kR^i$, —$CHF_2$, —$CHCl_2$, —$CHR^kN(R^k)C(O)NR^hR^i$, —$CHR^kC$-$(NOR^k)C(O)NR^hR^i$, —$CHR^kNHSO_2R^k$, —$CHR^kNH$-$P(O)(OR^i)(OR^h)$, —$CHR^kP(O)(OR^i)(OR^h)$ wherein $R^a$, $R^k$, $R^i$ and $R^h$ are hereinabove defined and;

$R^5$ is hydrogen or a suitable removable protecting group for a carboxylic acid;

which comprises reacting a compound of the formula:

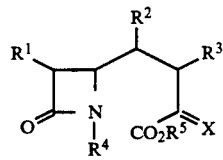

wherein $R^4$ is hydrogen or a suitable removable protecting group for an amide nitrogen; and X is oxygen, sulfur, a moiety of the formula $NR^6$ where $R^6$ is hydrogen, a straight or branched chain ($C_1$-$C_6$) lower alkyl, a moiety of the formula $NR^7$, where $R^7$ is OH, a straight or branched ($C_1$-$C_6$) lower alkoxy or silyloxy, or a moiety of the formula N—$NR^8R^9$ where $R^8$ and $R^9$ independently chosen from hydrogen, lower alkyl ($C_1$-$C_6$), benzyl, phenyl, $CO_2R^5$ where $R^5$ is as hereinbefore defined, or $R^8$ and $R^9$ together with the associated nitrogen form a 5 or 6 membered cycloalkyl ring; with a suitable acid.

2. A process for preparing a compound of the formula:

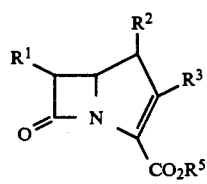

wherein:

$R^1$, $R^2$, $R^3$, and $R^5$ are defined in claim 1 which comprises;

(a) contacting a compound of the formula:

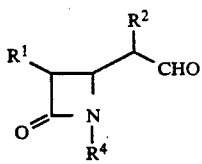

wherein:

$R^1$, $R^2$ and $R^4$ are as defined in claim 1 with a compound of the formula:

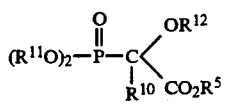

wherein:
$R^5$ is hereinbefore defined;
$R^{10}$ is a metal cation;
$R^{11}$ is alkyl or branched alkyl phenyl substituted alkyl group, phenyl, optionally substituted with 1-3 carbon groups;
$R^{12}$ is a substituted silyl group, an acyl group or an aralkylcarbonyl group to yield a compound of the formula:

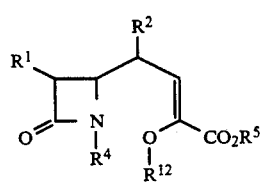

wherein:
$R^1$, $R^2$, $R^4$, $R^5$ and $R^{12}$ are hereinbefore defined;

(b) the compound of step a is contacted with an appropriate halogen source to give a compound of the formula:

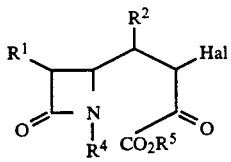

wherein
$R^1$, $R^2$, $R^4$ and $R^5$ are hereinbefore defined;

(c) the compound of step b is contacted with a reagent $R^3$—H where $R^3$ is hereinbefore defined to yield a compound of the formula:

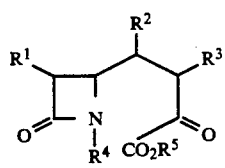

wherein:
$R^1$, $R^2$, $R^3$, $R^4$ and $R^5$ are hereinbefore defined;

(d) the compound of step c is contacted with a suitable acid to give a compound of the formula:

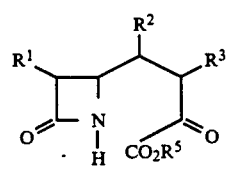

wherein:
$R^1$, $R^2$, $R^3$ and $R^5$ are hereinbefore defined;

(e) the compound of step d is contacted with a suitable acid to afford a compound of the formula:

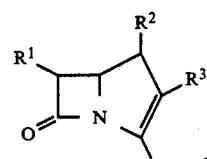

wherein:
$R^1$, $R^2$, $R^3$ and $R^5$ are hereinbefore defined.

* * * * *